United States Patent
Schweizer et al.

(10) Patent No.: US 7,608,756 B2
(45) Date of Patent: Oct. 27, 2009

(54) PROMOTERS FOR EPIDERMIS-SPECIFIC EXPRESSION OF DESIRED CODING SEQUENCES IN TRANSGENIC PLANTS

(75) Inventors: Patrick Schweizer, Ballenstedt (DE); Robert Dudler, Uster (CH); Paul Schulze-Lefert, Köln (DE); Ralph Panstruga, Aachen (DE)

(73) Assignees: IPK Institut für Pflanzengenetik und Kulturpflanzenforschung, Gatersleben (DE); Max-Planck-Gesellschaft zur Förderung der Wissenschaften E.V., München (DE); Universität Zürich, Zürich (CH)

( * ) Notice: Subject to any disclaimer, the term of this patent is extended or adjusted under 35 U.S.C. 154(b) by 0 days.

(21) Appl. No.: 10/574,740

(22) PCT Filed: Oct. 7, 2004

(86) PCT No.: PCT/EP2004/011214

§ 371 (c)(1),
(2), (4) Date: Jan. 22, 2007

(87) PCT Pub. No.: WO2005/035766

PCT Pub. Date: Apr. 21, 2005

(65) Prior Publication Data

US 2007/0300328 A1    Dec. 27, 2007

(30) Foreign Application Priority Data

Oct. 7, 2003    (DE) ................. 103 46 611

(51) Int. Cl.
*A01H 1/00* (2006.01)
*C12N 15/09* (2006.01)
*C12N 15/82* (2006.01)

(52) U.S. Cl. ............ 800/287; 800/278; 800/279; 800/298; 800/320; 800/317; 435/468; 435/69.1

(58) Field of Classification Search ............... None
See application file for complete search history.

(56) References Cited

OTHER PUBLICATIONS

Kim et al. Plant Molecular Biology, 1994 vol. 24, pp. 105-117.*
Mauch F. et al: "differential induction of distinct glutathione-S-transferase of wheat by xenobiotics and pathogen attack" Plant Physiol, vol. 102, 1993, pp. 1193-1201, XP002313139.
Xu F. et al: "tandemly duplicated safener induced glutathione s-transferase genes from *Triticum tauschii* contribute to genome and organe-specific expression in hexaploid wheat" Plant Physiol, vol. 130, 2002, pp. 362-373, XP002313140.

* cited by examiner

*Primary Examiner*—Medina A Ibrahim
(74) *Attorney, Agent, or Firm*—Knobbe Martens Olson & Bear LLP

(57) ABSTRACT

The invention relates to methods of producing transgenic plants including pathogen resistant plants with recombinant nucleic acid molecules comprising promoter regions which provides expression of a desired transgene in epidermis-specific manner, and transgenic plants produced by said methods.

17 Claims, 22 Drawing Sheets

Figure 1

GstA1 promoter

```
GACGCCGAAGTGGAGCCGACAGCCCCCAGGTCCCAAGCCCTCGGCAGACTAGATCACTAGCCCTGGATCGGCGAGGTGAC
TGGATGACGAGCAGCACCTGGTCTGGCGGGTGTTGGGCGAGTAGAACCAGGGGCGATGGCGACGCGCTGACCTTCTCCCC
TCACCGGCGATCTGCTCCTTCTGGGTGGGGGTCGCCGGCTGACGTTCTGTTGCGGGGTGGGGGTCGCCGGCTGGCGTTCT
GCTGCGGGGTGGGAGTCGCCGACCGGCGTGCTGCTGCTAGGACAATCGGTGAGGCCAGTTAGGTGCTAGCCGATCGATTG
GCGAAGAGATCCGAGTCCTGGGGAGATCAGTGAGGCCAGGTGCTATTTGGCCTATCAATTGGCCAGGTTCTGGGAACGGG
GCGTGGCGTGATCAACGAGGTGCTAGGCTGCTAGCTAGGGAACTGGATCCTGGAACGTGGAGGAGGCAAGTCCGGTATGC
TAAGTACTTTAACTTTCCTTCTTCACATCCACCTGATTCAGATTATTTTGATCTAAATTAACTTGCAAAAAATATATGTG
TGATATCCATCTACTATAATTGCTTACAATCAAAATTATATGTGATTTTTTTTAGTTTAGAAGATTTATATGCACAGTAA
ATCTGAATGTTCTTCACATGCATGATTTAGTTTAACTTTAAAGAGTTATACTAACTAGTCTTGATAAAGAGATCTTTTGG
AGCAACACCAAACCTCGTGAGGTGTTTTGCCTACGGAAAGGTTGTGCTATGTAATGATTATTATTAGGATCAAAGTTGTA
GGATAAACGTAAAACCTTCTCGATGTATCTTTTATACAACATTGTAGTTTAGTTATATATGGAGAGAGTGATTTAACACT
TTGTGTTTAAGAGTAGAATAAGTTATTCCACACTCTAGCCAAACGAACTATTTGGCAAATATCTCGCTAGCTGGTGAGAG
CCAGAGCCGTGGAAAGTCTGTCTTGCTATTAAGGCACAAGCATCAAACAGGAACATTTAGAGCCATGGAAAAGTGATGTG
TCGCCTACCAATGGGCCAACTGCTAGCGATGTAATAATAGCATCCAAGTTGATTTTTTATAGAACATGCAAGGCGTTGGC
AAGTGGGAAAATGATTGATCGCTGGCAAGCTTAACTCTCGGAACTTATAGCATTCAACTGAATCAGAACAAAGATTAAAA
AAAAATACATTTCCATCGATAGTGAAAAATTATTCAATTGAGTGACAACGAAAATCATATTGGAATGTACATTTACTTGT
TGATTTTAAATTAGAGGCATTTTTCTACCTTTTTTAGTTAATAAGATATGCATATACCCACCCTTAGTGTTTCGAGACA
ACGAGAGGGCACATTGCTTTTGGTGCTACCATCTCTCTCAAGCCTCAAATAAGTTGTGCGGACACGATTATCTTCCCGCG
TTGGAATATCGTGGCCTGGTAGAGCTAGCGAAAAATCTTCCATGTTGGAATATGTCGGCAGCCGGATAGCCGCCATGCAT
GTAAAGTCTCTTTTACCTTTACACTTGCTCAAGTGACACTGTATGTCGCCTACCACTTGCTAAATCAATGGGCCAACTGC
TAGCGACGTAATAGTAGCAAGTTGATTTACAGTGTTTTGCTACAGTTCTCTGACTTTGTTTCTTCATTTTAGACTAGCTG
ACTACTGTCGCTTACCTGCCTTCCCTTCTCCACGTTAGAGGATCCAGTTCTGATATTGAGACCTCGACGATGGGAGGAAG
GGCGCGATCGATGTGGAGTAATTTGAATTTCAAATCTATCTATCTGGGGTATATTGGTCCTTCACCGATGTTTGGGGGGC
TGTCGGAAATTGGTTCCGCGATCTACAAAAGTGAATGGAGGGAGTAGTTGTTTCTCCAATCCGTACCAACGCACGTGTTT
CTAACTAGTACTTACTTCCTTCGCACCACAATATGGAATAGAGGGAGTATCGATAAACTAACAAAGATGATTACTTACCC
GGTTTAAATGATTCAAGAGCTCATTTAATTTGGCACTCATCATTTCATATATCTTTTTTGGTAGAAATGAAATAAAGCAG
ATCTAGACACTAGCTAAAAAGTCGATGTAGCCTTGTTATTTCCTTGGGCCACGCGGGCCGGGTGTGGTGCTCCCTGCTCT
GTGTATAAATGGAGATCAACATCCAAGGCCTCCTCCCA
```

Figure 2

WIR1A intron

GTCAGTCGTCGGACGGTGTCCGTTCATTTCCTCCCCATTTTTGTAATTGATTAACTTGTTATACATGCTGACCTCGACCTGCT
GAATAACGTCCGTCCATGGTTTCCCGTCCAGGCACC

Figure 3

GstA1 promoter with WIR1a exon/intron:

```
GACGCCGAAGTGGAGCCGACAGCCCCCAGGTCCCAAGCCCTCGGCAGACTAGATCACTAGCCCTGGATCGGCGAGGTGAC
TGGATGACGAGCAGCACCTGGTCTGGCGGGTGTTGGGCGAGTAGAACCAGGGGCGATGGCGACGCGCTGACCTTCTCCCC
TCACCGGCGATCTGCTCCTTCTGGGTGGGGGTCGCCGGCTGACGTTCTGTTGCGGGGTGGGGGTCGCCGGCTGGCGTTCT
GCTGCGGGGTGGGAGTCGCCGACCGGCGTGCTGCTGCTAGGACAATCGGTGAGGCCAGTTAGGTGCTAGCCGATCGATTG
GCGAAGAGATCCGAGTCCTGGGGAGATCAGTGAGGCCAGGTGCTATTTGGCCTATCAATTGGCCAGGTTCTGGGAACGGG
GCGTGGCGTGATCAACGAGGTGCTAGGCTGCTAGCTAGGGAACTGGATCCTGGAACGTGGAGGAGGCAAGTCCGGTATGC
TAAGTACTTTAACTTTCCTTCTTCACATCCACCTGATTCAGATTATTTTGATCTAAATTAACTTGCAAAAAATATATGTG
TGATATCCATCTACTATAATTGCTTACAATCAAAATTATATGTGATTTTTTTTAGTTTAGAAGATTTATATGCACAGTAA
ATCTGAATGTTCTTCACATGCATGATTTAGTTTAACTTTAAAGAGTTATACTAACTAGTCTTGATAAAGAGATCTTTTGG
AGCAACACCAAACCTCGTGAGGTGTTTTGCCTACGGAAAGGTTGTGCTATGTAATGATTATTATTAGGATCAAAGTTGTA
GGATAAACGTAAAACCTTCTCGATGTATCTTTTATACAACATTGTAGTTTAGTTATATATGGAGAGAGTGATTTAACACT
TTGTGTTTAAGAGTAGAATAAGTTATTCCACACTCTAGCCAAACGAACTATTTGGCAAATATCTCGCTAGCTGGTGAGAG
CCAGAGCCGTGGAAAGTCTGTCTTGCTATTAAGGCACAAGCATCAAACAGGAACATTTAGAGCCATGGAAAAGTGATGTG
TCGCCTACCAATGGGCCAACTGCTAGCGATGTAATAATAGCATCCAAGTTGATTTTTTATAGAACATGCAAGGCGTTGGC
AAGTGGGAAATGATTGATCGCTGGCAAGCTTAACTCTCGGAACTTATAGCATTCAACTGAATCAGAACAAAGATTAAAA
AAAAATACATTTCCATCGATAGTGAAAAATTATTCAATTGAGTGACAACGAAAATCATATTGGAATGTACATTTACTTGT
TGATTTTAAATTAGAGGCATTTTTCTACCTTTTTTAGTTAATAAGATATGCATATACCCACCCTTAGTGTTTTCGAGACA
ACGAGAGGGCACATTGCTTTTGGTGCTACCATCTCTCTCAAGCCTCAAATAAGTTGTGCGGACACGATTATCTTCCCGCG
TTGGAATATCGTGGCCTGGTAGAGCTAGCGAAAAATCTTCCATGTTGGAATATGTCGGCAGCCGGATAGCCGCCATGCAT
GTAAAGTCTCTTTTACCTTTACACTTGCTCAAGTGACACTGTATGTCGCCTACCACTTGCTAAATCAATGGGCCAACTGC
TAGCGACGTAATAGTAGCAAGTTGATTTACAGTGTTTTGCTACAGTTCTCTGACTTTGTTTCTTCATTTTAGACTAGCTG
ACTACTGTCGCTTACCTGCCTTCCCTTCTCCACGTTAGAGGATCCAGTTCTGATATTGAGACCTCGACGATGGGAGGAAG
GGCGCGATCGATGTGGAGTAATTTGAATTTCAAATCTATCTATCTGGGGTATATTGGTCCTTCACCGATGTTTGGGGGGC
TGTCGGAAATTGGTTCCGCGATCTACAAAAGTGAATGGAGGGAGTAGTTGTTTCTCCAATCCGTACCAACGCACGTGTTT
CTAACTAGTACTTACTTCCTTCGCACCACAATATGGAATAGAGGGAGTATCGATAAACTAACAAAGATGATTACTTACCC
GGTTTAAATGATTCAAGAGCTCATTTAATTTGGCACTCATCATTTCATATATCTTTTTTGGTAGAAATGAAATAAAGCAG
ATCTAGACACTAGCTAAAAAGTCGATGTAGCCTTGTTATTTCCTTGGGCCACGCGGGCCGGGTGTGGTGCTCCCTGCTCT
GTGTATAAATGGAGATCAACATCCAAGGCCTCCTCCCACACACACACGCTACAGAGCAGAGCAGAGTCTTGCTCCAGTAT
CTGCCCTCTCCTGCCTGCCTGTAGAGCATCCATCACGTGAAGTTCACGGACAAACTACGTACACAGGCAGCTAGCTCTCG
AAACCTCGCTCGAAACGCACCTGCAGATCGCTCTCTTCGTCGTCGTCGCCGCGATCATCATCAACAGCTCCGTCTGCCTT
GGAGCCACGGCCGTCCACGACGCCGCCGCCTCAGGTCAGTCGTCGGACGGTGTCCGTTCATTTCCTCCCCATTTTTGTAA
TTGATTAACTTGTTATACATGCTGACCTCGACCTGCTGAATAACGTCCGTCCATGGTTTCCCGTCCAGGCACC
```

Figure 4

TaPERO cDNA:

```
ACCACCACACCACTCCACCAGTAAGAAGTGCAGCAGGTAGCTAGTAAGCCGGCGTAGCTTTGCTCTTGCAGCTAGCTAGC
TAACCATGGCCGCCTCTGCCTCTTGCCTTTCTCTTGTGGTGCTCGTGGCTCTGGCCACGGCGGCGTCGGCGCAGCTGTCA
CCGACCTTCTACGACACGTCCTGCCCCAGGGCCCTGGCCATCATCAAGAGTGGCGTCATGGCCGCCGTGAGCAGCGACCC
TCGGATGGGCGCGTCGCTGCTCCGGCTGCACTTCCACGACTGCTTCGTCCAAGGCTGCGACGCGTCTGTTTTGCTGTCTG
GCATGGAACAAAATGCTATCCCGAACGCGGGGTCGCTGAGGGGCTTCGGCGTCATCGACAGCATCAAGACGCAGATCGAG
GCCATCTGCAATCAGACCGTCTCCTGCGCCGACATCCTCACCGTCGCCGCCCGTGACTCCGTTGTAGCCCTCGGAGGGCC
GTCATGGACAGTCCCTCTGGGGAGAAGAGATTCCACAGATGCAAACGAGGCGGCGGCAAACAGCGACCTGCCAGGCTTTA
CATCTAGCCGGTCAGATCTTGAGCTGGCATTCAGAAACAAGGGCCTCCTTACGATCGACATGGTGGCCCTCTCGGGCGCG
CACACCATCGGCCAGGCGCAGTGTGGGACCTTTAAGGACAGGATCTACAATGAGACTAACATCGACACGGCCTTCGCCAC
ATCTCTCCGGGCCAACTGCCCCAGGTCAAACGGCGACGGGAGCCTGGCGAACCTGGACACGACGACGGCCAACACGTTCG
ATAACGCCTACTACACCAACCTCATGTCACAGAAGGGGCTCCTGCACTCGGACCAGGTGCTGTTCAACAACGACACCACC
GACAACACTGTCCGGAACTTTGCGTCGAACCCAGCGGCGTTCAGCAGCGCCTTCACGACCGCCATGATCAAGATGGGCAA
CATCGCGCCGAAGACAGGCACGCAGGGGCAGATCAGGCTCAGCTGCTCCAGGGTGAACTCGTGATTGATAGACGAGTTAC
TGCATACTAGCCAGCACGACACGTACGTGAATGAATAAGGCCACAGAACCAGTGGCCAATATAAATACCAGCTCTTGAAA
CCGTGTATTTTATGTACGAGTAGCAGCAAATCATGCATGCATCTACACATATATATGTAACGATCGAATTCCCACTTTCT
CATGCAAAGGCATGGAGAATTACTATCAATCTTAGTTATACGTGTA
```

Figure 5a:

characteristics of pPS41:

| | |
|---|---|
| Total length: | 7011 bp |
| vector Backbone: pBluescript SK+, | entire construct between XhoI and SacI restriction sites |
| GstA1 promoter; | 694-2891 |
| Transcription start: | 2892 |
| GstA1 5' UTR | 2892-2988 |
| WIR1 5' UTR (part) | 2989-3034 |
| WIR1 part of 5' CDS + Intron | 3035-3246 |
| TAPERO cDNA | 3264-4509 |
| ATG TAPERO | 3348 |
| Stop codon: | 4284 |
| Poly(A) | 4510-4514 |
| CamV 35S Terminator: | 4576-4776 |

```
CTAAATTGTAAGCGTTAATATTTTGTTAAAATTCGCGTTAAATTTTTGTTAAATCAGCTCATTTTTTAACCAATAGGCCG
AAATCGGCAAAATCCCTTATAAATCAAAAGAATAGACCGAGATAGGGTTGAGTGTTGTTCCAGTTTGGAACAAGAGTCCA
CTATTAAAGAACGTGGACTCCAACGTCAAAGGGCGAAAAACCGTCTATCAGGGCGATGGCCCACTACGTGAACCATCACC
CTAATCAAGTTTTTTGGGGTCGAGGTGCCGTAAAGCACTAAATCGGAACCCTAAAGGGAGCCCCCGATTTAGAGCTTGAC
GGGGAAAGCCGGCGAACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCCATTCAGGCTGCG
CAACTGTTGGGAAGGGCGATCGGTGCGGGCCTCTTCGCTATTACGCCAGCTGGCGAAAGGGGGATGTGCTGCAAGGCGAT
TAAGTTGGGTAACGCCAGGGTTTTCCCAGTCACGACGTTGTAAAACGACGGCCAGTGAGCGCGCGTAATACGACTCACTA
TAGGGCGAATTGGGTACCGGGCCCCCCCTCGAGTCTAGAACTAGTGGATCCCCGACGCCGAAGTGGAGCCGACAGCCCCC
AGGTCCCAAGCCCTCGGCAGACTAGATCACTAGCCCTGGATCGGCGAGGTGACTGGATGACGAGCAGCACCTGGTCTGGC
GGGTGTTGGGCGAGTAGAACCAGGGGCGATGGCGACGCGCTGACCTTCTCCCCTCACCGGCGATCTGCTCCTTCTGGGTG
GGGGTCGCCGGCTGACGTTCTGTTGCGGGGTGGGGGTCGCCGGCTGGCGTTCTGCTGCGGGGTGGGAGTCGCCGACCGGC
GTGCTGCTGCTAGGACAATCGGTGAGGCCAGTTAGGTGCTAGCCGATCGATTGGCGAAGAGATCCGAGTCCTGGGGAGAT
CAGTGAGGCCAGGTGCTATTTGGCCTATGTAATGATTATTATTAGGATCAAAGTTGTAGGATAAACGTAAAACCTTCTCGATGTA
TCTTTTATACAACATTGTAGTTTAGTTATATATGGAGAGAGTGATTTAACACTTTGTGTTTAAGAGTAGAATAAGTTATT
CCACACTCTAGCCAAACGAACTATTTGGCAAATATCTCGCTAGCTGGTGAGAGCCAGAGCCGTGGAAAGTCTGTCTTGCT
ATTAAGGCACAAGCATCAAACAGGAACATTTAGAGCCATGGAAAAGTGATGTGTCGCCTACCAATGGGCCAACTGCTAGC
GATGTAATAATAGCATCCAAGTTGATTTTTTATAGAACATGCAAGGCGTTGGCAAGTGGGAAAATGATTGATCGCTGGCA
AGCTTAACTCTCGGAACTTATAGCATTCAACTGAATCAGAACAAAGATTAAAAAAAATACATTTCCATCGATAGTGAAA
AATTATTCAATTGAGTGACAACGAAAATCATATTGGAATGTACATTTACTTGTTGATTTTAAATTAGAGGCATTTTTCTA
CCTTTTTAGTTAATAAGATATGCATATACCCACCCTTAGTGTTTTCGAGACAACGAGAGGGCACATTGCTTTTGGTGCT
ACCATCTCTCTCAAGCCTCAAATAAGTTGTGCGGACACGATTATCTTCCCGCGTTGGAATATCGTGGCCTGGTAGAGCTA
GCGAAAAATCTTCCATGTTGGAATATGTCGGCAGCCGGATAGCCGCCATGCATGTAAAGTCTCTTTTACCTTTACACTTG
CTCAAGTGACACTGTATGTCGCCTACCACTTGCTAAATCAATGGGCCAACTGCTAGCGACGTAATAGTAGCAAGTTGATT
TACAGTGTTTTGCTACAGTTCTCTGACTTTGTTTCTTCATTTTAGACTAGCTGACTACTGTCGCTTACCTGCCTTCCCTT
CTCCACGTTAGAGGATCCAGTTCTGATATTGAGACCTCGACGATGGGAGGAAGGGCGCGATCGATGTGGAGTAATTTGAA
TTTCAAATCTATCTATCTGGGGTATATTGGTCCTTCACCGATGTTTGGGGGGCTGTCGGAAATTGGTTCCGCGATCTACA
AAAGTGAATGGAGGGAGTAGTTGTTTCTCCAATCCGTACCAACGCACGTGTTTCTAACTAGTACTTACTTCCTTCGCACC
ACAATATGGAATAGAGGGAGTATCGATAAACTAACAAAGATGATTACTTACCCGGTTTAAATGATTCAAGAGCTCATTTA
ATTTGGCACTCATCATTTCATATATCTTTTTTGGTAGAAATGAAATAAAGCAGATCTAGACACTAGCTAAAAAGTCGATG
TAGCCTTGTTATTTCCTTGGGCCACGCGGGCCGGGTGTGGTGCTCCCTGCTCTGTGTATAAATGGAGATCAACATCCAAG
GCCTCCTCCCACACACACACGCTACAGAGCAGAGCAGAGTCTTGCTCCAGTATCTGCCCTCTCCTGCCTGCCTGTAGAGC
ATCCATCACGTGAAGTTCACGGACAAACTACGTACACAGGCAGCTAGCTCTCGAAACCTCGCTCGAAACGCACCTGCAGA
TCGCTCTCTTCGTCGTCGTCGCCGCGATCATCATCAACAGCTCCGTCTGCCTTGGAGCCACGGCCGTCCACGACGCCGCC
GCCTCAGGTCAGTCGTCGGACGGTGTCCGTTCATTTCCTCCCCATTTTTGTAATTGATTAACTTGTTATACATGCTGACC
TCGACCTGCTGAATAACGTCCGTCCATGGTTTCCCGTCCAGGCACCCCGGGCTGCAGGAATTCACCACCACACCACTCCA
CCAGTAAGAAGTGCAGCAGGTAGCTAGTAAGCGACTAGCCGGCGTAGCTTTGCTCTTGCAGCTAGCTAGCTAACCATGGCCGCCTCT
GCCTCTTGCCTTTCTCTTGTGGTGCTCGTGGCTCTGGCCACGGCGGCGTCGGCGCAGCTGTCACCGACCTTCTACGACAC
GTCCTGCCCCAGGGCCCTGGCCATCATCAAGAGTGGCGTCATGGCCGCCGTGAGCAGCGACCCTCGGATGGGCGCGTCGC
TGCTCCGGCTGCACTTCCACGACTGCTTCGTCCAAGGCTGCGACGCGTCTGTTTTGCTGTCTGGCATGGAACAAAATGCT
ATCCCGAACGCGGGGTCGCTGAGGGGCTTCGGCGTCATCGACAGCATCAAGACGCAGATCGAGGCCATCTGCAATCAGAC
CGTCTCCTGCGCCGACATCCTCACCGTCGCCGCCCGTGACTCCGTTGTAGCCCTCGGAGGGCCGTCATGGACAGTCCCTC
TGGGGAGAAGAGATTCCACAGATGCAAACGAGGCGGCGGCAAACAGCGACCTGCCAGGCTTTACATCTAGCCGGTCAGAT
CTTGAGCTGGCATTCAGAAACAAGGGCCTCCTTACGATCGACATGGTGGCCCTCTCGGGCGCGCACACCATCGGCCAGGC
GCAGTGTGGGACCTTTAAGGACAGGATCTACAATGAGACTAACATCGACACGGCCTTCGCCACATCTCTCCGGGCCAACT
```

```
GCCCCAGGTCAAACGGCGACGGGAGCCTGGCGAACCTGGACACGACGACGGCCAACACGTTCGATAACGCCTACTACACC
AACCTCATGTCACAGAAGGGGCTCCTGCACTCGGACCAGGTGCTGTTCAACAACGACACCACCGACAACACTGTCCGGAA
CTTTGCGTCGAACCCAGCGGCGTTCAGCAGCGCCTTCACGACCGCCATGATCAAGATGGGCAACATCGCGCCGAAGACAG
GCACGCAGGGGCAGATCAGGCTCAGCTGCTCCAGGGTGAACTCGTGATTGATAGACGAGTTACTGCATACTAGCCAGCAC
GACACGTACGTGAATGAATAAGGCCACAGAACCAGTGGCCAATATAAATACCAGCTCTTGAAACCGTGTATTTTATGTAC
GAGTAGCAGCAAATCATGCATGCATCTACACATATATATGTAACGATCGAATTCCCACTTTCTCATGCAAAGGCATGGAG
AATTACTATCAATCTTAGTTATACGTGTATAAAAAGCGGCCGCGAATTCGATATCAAGCTTATCGATACCGTCGACCTCG
ACCTGCAGGCATGCCCGCTGAAATCACCAGTCTCTCTCTACAAATCTATCTCTCTATAATAATGTGTGAGTAGTTCCC
AGATAAGGGAATTAGGGTTCTTATAGGGTTTCGCTCATGTGTTGAGCATATAAGAAACCCTTAGTATGTATTTGTATTTG
TAAAATACTTCTATCAATAAAATTTCTAATTCCTAAAACCAAAATCCAGGGGTACCGAGCTCGAATTCTAGTCTACGCGG
CCGCGAGCTCCAGCTTTTGTTCCCTTTAGTGAGGGTTAATTGCGCGCTTGGCGTAATCATGGTCATAGCTGTTTCCTGTG
TGAAATTGTTATCCGCTCACAATTCCACACAACATACGAGCCGGAAGCATAAAGTGTAAAGCCTGGGGTGCCTAATGAGT
GAGCTAACTCACATTAATTGCGTTGCGCTCACTGCCCGCTTTCCAGTCGGGAAACCTGTCGTGCCAGCTGCATTAATGAA
TCGGCCAACGCGCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATACCTGTCCGCCTTTCTCCCTTCGGG
AAGCGTGGCGCTTTCTCATAGCTCACGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGAGTCCAACCCGGTAAGACACGACTTA
TCGCCACTGGCAGCAGCCACTGGTAACAGGATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGCTGAAGCCAGTTACCTTCGGAAAAAGAGTTG
GTAGCTCTTGATCCGGCAAACAAACCACCGCTGGTAGCGGTGGTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTGTCTATTTCGTTCATCC
ATAGTTGCCTGACTCCCCGTCGTGTAGATAACTACGATACGGGAGGGCTTACCATCTGGCCCCAGTGCTGCAATGATACC
GCGAGACCCACGCTCACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAGTTAATAGTTTGCGC
AACGTTGTTGCCATTGCTACAGGCATCGTGGTGTCACGCTCGTCGTTTGGTATGGCTTCATTCAGCTCCGGTTCCCAACG
ATCAAGGCGAGTTACATGATCCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCATGCCATCCGTAAGATGCTTT
TCTGTGACTGGTGAGTACTCAACCAAGTCATTCTGAGAATAGTGTATGCGGCGACCGAGTTGCTCTTGCCCGGCGTCAAT
ACGGGATAATACCGCGCCACATAGCAGAACTTTAAAAGTGCTCATCATTGGAAAACGTTCTTCGGGGCGAAAACTCTCAA
GGATCTTACCGCTGTTGAGATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCAC
``` continuation Figure 5a

Figure 6

Germin 9f-2.8:

```
AGCTTATTACATAGCAAGCATGGGGTACTCCAAAACCCTAGTAGCTGGCCTGTTCGCAATGCTGTTACTAGCTCCGGCCG
TCTTGGCCACCGACCCAGACCCTCTCCAGGACTTCTGTGTCGCCGACCTCGACGGCAAGGCGGTCTCGGTGAACGGGCAC
ACGTGCAAGCCCATGTCGGAGGCCGGCGACGACTTCCTCTTCTCGTCCAAGTTGGCCAAGGCCGGCAACACGTCCACCCC
GAACGGCTCCGCCGTGACGGAGCTCGACGTGGCCGAGTGGCCCGGTACCAACACGCTGGGTGTGTCCATGAACCGCGTGG
ACTTTGCTCCCGGAGGCACCAACCCACCACACATCCACCCGCGTGCCACCGAGATCGGCATCGTGATGAAAGGTGAGCTT
CTCGTGGGAATCCTTGGCAGCCTCGACTCCGGGAACAAGCTCTACTCGAGGGTGGTGCGCGCCGGAGAGACGTTCCTCAT
CCCACGGGGCCTCATGCACTTCCAGTTCAACGTCGGTAAGACCGAGGCCTCCATGGTCGTCTCCTTCAACAGCCAGAACC
CCGGCATTGTCTTCGTGCCCCTCACGCTCTTCGGCTCCAACCCGCCCATCCCAACGCGGGTGCTCACCAAGGCACTCCGG
GTGGAGGCCAGGGTCGTGGAACTTCTCAAGTCCAAGTTTGCCGCTGGGTTTAATTTCTAGGAGCCTTCCCTGAAATGAT
AATTATATAATTCCATATATGCATGC
```

Figure 7a characteristics of pPS24:

| | |
|---|---|
| total length | 6452 bp |
| vector Backbone: pBluescript SK+, | entire construct between XhoI and SacI restriction sites |
| GstA1 promoter | 694-2891 |
| Transcription start: | 2892 |
| GstA1 5' UTR | 2892-2988 |
| WIR1 5' UTR (part) | 2989-3034 |
| WIR1 part of 5' CDS + Intron | 3035-3246 |
| Germin 9f-2.8 Gen | 3258-4003 |
| ATG Germin | 3277 |
| Stop codon: | 3949 |
| CaMV 35S Terminator: | 4017-4210 |

Sequenz:
```
CTAAATTGTAAGCGTTAATATTTTGTTAAAATTCGCGTTAAATTTTTGTTAAATCAGCTCATTTTTTAACCAATAGGCCG
AAATCGGCAAAATCCCTTATAAATCAAAAGAATAGACCGAGATAGGGTTGAGTGTTGTTCCAGTTTGGAACAAGAGTCCA
CTATTAAAGAACGTGGACTCCAACGTCAAAGGGCGAAAAACCGTCTATCAGGGCGATGGCCCACTACGTGAACCATCACC
CTAATCAAGTTTTTTGGGGTCGAGGTGCCGTAAAGCACTAAATCGGAACCCTAAAGGGAGCCCCCGATTTAGAGCTTGAC
GGGGAAAGCCGGCGAACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCCATTCAGGCTGCG
CAACTGTTGGGAAGGGCGATCGGTGCGGGCCTCTTCGCTATTACGCCAGCTGGCGAAAGGGGGATGTGCTGCAAGGCGAT
TAAGTTGGGTAACGCCAGGGGTTTTCCCAGTCACGACGTTGTAAAACGACGGCCAGTGAGCGCGCGTAATACGACTCACTA
TAGGGCGAATTGGGTACCGGGCCCCCCCTCGAGTCTAGAACTAGTGGATCCCCGACGCCGAAGTGGAGCCGACAGCCCCC
AGGTCCCAAGCCCTCGGCAGACTAGATCACTAGCCCTGGATCGGCGAGGTGACTGGATGACGAGCAGCACCTGGTCTGGC
GGGTGTTGGGCGAGTAGAACCAGGGGCGATGGCGACGCGCTGACCTTCTCCCCTCACCGGCGATCTGCTCCTTCTGGGTG
GGGGTCGCCGGCTGACGTTCGTTGCGGGTGGGGGTCGCCGGCTGGCGTTCTGCTGCGGGGTGGGAGTCGCCGACCGGC
GTGCTGCTGCTAGGACAATCGGTGAGGCCAGTTAGGTGCTAGCCGATCGATTGGCGAAGAGATCCGAGTCCTGGGGAGAT
CAGTGAGGCCAGGTGCTATTTGGCCTATCAATTGGCCAGGTTCTGGGAACGGGGCGTGGCGTGATCAACGAGGTGCTAGG
CTGCTAGCTAGGGAACTGGATCCTGGAACGTGGAGGAGGCAAGTCCGGTATGCTAAGTACTTTAACTTTCCTTCTTCACA
TCCACCTGATTCAGATTATTTTGATCTAAATTAACTTGCAAAAAATATATGTGTGATATCCATCTACTATAATTGCTTAC
AATCAAAATTATATGTGATTTTTTTTAGTTTAGAAGATTTATATGCACAGTAAATCTGAATGTTCTTCACATGCATGATT
TAGTTTAACTTTAAAGAGTTATACTAACTAGTCTTGATAAAGAGATCTTTTGGAGCAACACCAAACCTCGTGAGGTGTTT
TGCCTACGGAAAGGTTGTGCTATGTAATGATTATTATTAGGATCAAAGTTGTAGGATAAACGTAAAACCTTCTCGATGTA
TCTTTTATACAACATTGTAGTTTAGTTATATATGGAGAGAGTGATTTAACACTTTGTGTTTAAGAGTAGAATAAGTTATT
CCACACTCTAGCCAAACGAACTATTTGGCAAATATCTCGCTAGCTGGTGAGAGCCAGAGCCGTGGAAAGTCTGTCTTGCT
ATTAAGGCACAAGCATCAAACAGGAACATTTAGAGCCATGGAAAAGTGATGTGTCGCCTACCAATGGGCCAACTGCTAGC
ATGTAATAATAGCATCCAAGTTGATTTTTTATAGAACATGCAAGGCGTTGGCAAGTGGGAAAATGATTGATCGCTGGCA
AGCTTAACTCTCGGAACTTATAGCATTCAACTGAATCAGAACAAAGATTAAAAAAAAATACATTTCCATCGATAGTGAAA
AATTATTCAATTGAGTGACAACGAAATCATATTGGAATGTACATTTACTTGTTGATTTTAAATTAGAGGCATTTTTCTA
CCTTTTTTAGTTAATAAGATATGCATATACCCACCCTTAGTGTTTCGAGACAACGAGAGGGCACATTGCTTTTGGTGCT
ACCATCTCTCTCAAGCCTCAAATAAGTTGTGCGGACACGATTATCTTCCCGCGTTGGAATATCGTGGCCTGGTAGAGCTA
GCGAAAAATCTTCCATGTTGGAATATGTCGGCAGCCGGATAGCCGCCATGCATGTAAAGTCTCTTTTACCTTTACACTTG
CTCAAGTGACACTGTATGTCGCCTACCACTTGCTAAATCAATGGGCCAACTGCTAGCGACGTAATAGTAGCAAGTTGATT
TACAGTGTTTTGCTACAGTTCTCTGACTTTGTTTCTTCATTTTAGACTAGCTGACTACTGTCGCTTACCTGCCTTCCCTT
CTCCACGTTAGAGGATCCAGTTCTGATATTGAGACCTCGACGATGGGAGGAAGGGCGCGATCGATGTGGAGTAATTTGAA
TTTCAAATCTATCTATCTGGGGTATATTGGTCCTTCACCGATGTTTGGGGGGCTGTCGGAAATTGGTTCCGCGATCTACA
AAAGTGAATGGAGGGAGTAGTTGTTTCTCCAATCCGTACCAACGCACGTGTTTCTAACTAGTACTTACTTCCTTCGCACC
ACAATATGGAATAGAGGGAGTATCGATAAACTAACAAAGATGATTACTTACCCGGTTTAAATGATTCAAGAGCTCATTTA
ATTTGGCACTCATCATTTCATATATCTTTTTTGGTAGAAATGAAATAAAGCAGATCTAGACACTAGCTAAAAAGTCGATG
TAGCCTTGTTATTTCCTTGGGCCACGCGGGCCGGGTGTGGTGCTCCCTGCTCTGTGTATAAATGGAGATCAACATCCAAG
GCCTCCTCCCACACACACACGCTACAGAGCAGAGCAGAGTCTTGCTCCAGTATCTGCCCTCTCCTGCCTGCCTGTAGAGC
ATCCATCACGTGAAGTTCACGGACAAACTACGTACACAGGCAGCTAGCTCTCGAAACCTCGCTCGAAACGCACCTGCAGA
TCGCTCTCTTCGTCGTCGTCGCCGCGATCATCATCAACAGCTCCGTCTGCCTTGGAGCCACGGCCGTCCACGACGCCGCC
GCCTCAGGTCAGTCGTCGGACGGTGTCCGTTCATTTCCTCCCCATTTTTGTAATTGATTAACTTGTTTATACATGCTGACC
TCGACCTGCTGAATAACGTCCGTCCATGGTTTCCCGTCCAGGCACCCCGGGGGATCCAGCTTATTACATAGCAAGCATGG
GGTACTCCAAAACCGTAGTAGCTGGCCTGTTCGCAATGCTGTTACTAGCTCCGGCCGTCTTGGCCACCGACCCAGACCCT
CTCCAGGACTTCTGTGTCGCCGACCTCGACGGCAAGGCGGTCTCGGTGAACGGGCACACGTGCAAGCCCATGTCGGAGGC
CGGCGACGACTTCCTCTTCTCGTCCAAGTTGGCCAAGGCCGGCAACACGTCCACCCCGAACGGCTCCGCCGTGACGGAGC
TCGACGTGGCCGAGTGGCCCGGTACCAACACGCTGGGTGTGTCCATGAACCGCGTGGACTTTGCTCCCGGAGGCACCAAC
CCACCACACATCCACCCGCGTGCCACCGAGATCGGCATCGTGATGAAAGGTGAGCTTCTCGTGGGAATCCTTGGCAGCCT
CGACTCCGGGAACAAGCTCTACTCGAGGGTGGTGCGCGCCGGAGAGACGTTCCTCATCCCACGGGCCTCATGCACTTCC
AGTTCAACGTCGGTAAGACCGAGGCCTCCATGGTCGTCTCCTTCAACAGCCAGAACCCCGGCATTGTCTTCGTGCCCCTC
ACGCTCTTCGGCTCCAACCCCGCCCATCCCAACGCCGGTGCTCACCAAGGCACTCCGGGTGGAGGCCAGGGTCGTGGAACT
TCTCAAGTCCAAGTTTGCCGCTGGGTTTTAATTTCTAGGAGCCTTCCCTGAAATGATAATTATATAATTCCATATATGCA
```

```
TGCCTGCAGGCATGCCCGCTGAAATCACCAGTCTCTCTCTACAAATCTATCTCTCTCTATAATAATGTGTGAGTAGTTCC
CAGATAAGGGAATTAGGGTTCTTATAGGGTTTCGCTCATGTGTTGAGCATATAAGAAACCCTTAGTATGTATTTGTATTT
GTAAAATACTTCTATCAATAAAATTTCTAATTCCTAAAACCAAAATCCAGGGGTACCGAGCTCGAATTCTAGTCTACGCG
GCCGCGAGCTCCAGCTTTTGTTCCCTTTAGTGAGGGTTAATTGCGCGCTTGGCGTAATCATGGTCATAGCTGTTTCCTGT
GTGAAATTGTTATCCGCTCACAATTCCACACAACATACGAGCCGGAAGCATAAAGTGTAAAGCCTGGGGTGCCTAATGAG
TGAGCTAACTCACATTAATTGCGTTGCGCTCACTGCCCGCTTTCCAGTCGGGAAACCTGTCGTGCCAGCTGCATTAATGA
ATCGGCCAACGCGCGGGAGAGGCGGTTTGCGTATTGGGCGCTCTTCCGCTTCCTCGCTCACTGACTCGCTGCGCTCGGT
CGTTCGGCTGCGGCGAGCGGTATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTACCGGATACCTGTCCGCCTTTCTCCCTTCGG
GAAGCGTGGCGCTTTCTCATAGCTCACGCTGTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCGTCTTGAGTCCAACCCGGTAAGACACGACTT
ATCGCCACTGGCAGCAGCCACTGGTAACAGGATTAGCAGAGCGAGGTATGTAGGCGGTGCTACAGAGTTCTTGAAGTGGT
GGCCTAACTACGGCTACACTAGAAGGACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTTTTAAATCAATCTAAAGTATA
TATGAGTAAACTTGGTCTGACAGTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATCTGGCCCCAGTGCTGCAATGATAC
CGCGAGACCCACGCTCACCGGCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCAC
``` continuation figure 7a

Figure 8

TaMlo inverted repeats and MlaI Intron:

```
CCACTGTCCACACGAAATGTGCCATCTGAAACGCGTTCTGGAACAGCGTCAGGTGTATGAAGAAGAGGACCCAGTCGGGG
CGGTGGAACCAGAAGAACTTGTTGCTGGGCTCGACCACGGGTGCCCCCTTGATGACGCTCGACCGGTCCTGGATCTCCAG
GGCCATCTCCATGATGATCATCTCTAGCTTGGTTCCAACACACAAGAGGATGATGAGAGGGATGAAAGAAACCCAGGTGA
GTGTGCCGATCCCGTCGATATCAAGGAAGAGGGTGAGGATCGCCACAGCCCACAGCGGGAGGCTGCGAAAAGAGGCCAAA
TGTGTCAAGATCATGCAACAAGGACCAGCAGGGGCAAAGACCATGACGCAGCAAACTGATAGTATTGTATCATATGGAAG
CTAAGCAATATCATATGGAGCCTGACGACACTCGTGCCGAATTCGATTCGTGAATTTCTAGAGAACAAAAGGTATGCATC
AATTTAGAAAAAAGTACACTATTATGTGATGTTTGTTTCCTATGCTAGTGGAACGGATTAGAATTTTTTTTTCATTAAGG
TCACCTTTACTGGCATAAGCAGTTCACACTAAACGGTAAACCTTATAGGTGAAAATTTTCAGGCATATATATATATATAT
ATATATATATATGTTTGATTCTTTCCGGCTTAACAAAATAATTAGCAAGTACTTCTTGTTGCATTTGTTCCAACGGCTGA
ATTTATTGGCATCGGTCCAAGAAATCCATCTAAATGTTTTACATTTCACCAAAGTGTGTGTCATGACAGATGTAACAAAT
AATAAACCAAAAGGAGAGGAAGGAAAGAGGAAGATAAATGTTACAAAAATTTAAATCAAACTTATTTCTACCTTTCTCCT
TACCTACCCAGTTTAAAAACACATATTATATTTTAAAGAGAGGCAACATGCGCCAAAGGCTACCCTTGAAAATTCCTAAA
ATATTGTACATTTGACTGATGACCAAACAAAAAGTTAAATTGTCTCTTCCTTATCACATTATATTTCCATGCATGCCTTT
TTCTGGAAACTTACTATCAGCAAAATTTAGATGAAAGGATAATGCCACATAATTTCAGTCTCCAAGAGATTTGTTAGTTG
TCATATATTAAATTGGTGGGCCAATCTATTCCTGGGTCTTTTTATGTATCTACTTGACCATTTGAACTTCTGTAGTTAAT
TGTATTCTATGAATGATCACTCATCCAAAAACTTGTTATTTGTGTTTTACTCTGTTGAATCTTGAATATTTATTCATTTT
GTTCATCATACGATTGGAGGCCCATAATAGATGCTTAATGAGAGTAAGATTATCGATCTCCAAACACATGCTTCTTACTA
GTGTTGAATATATACCCTTTTAGATGTATAGTTCAACCCATAGATTCATATGACCCTCAGCTTTCTGATGTGTATGTATG
ACCTTACACTGACACTCTGAACTAATGTAGGTATCTTGTCCTGCAGGAATTCGGCACGAGTGTCGTCAGGCTCCATATGA
TATTGCTTAGCTTCCATATGATACAATACTATCAGTTTGCTGCGTCATGGTCTTTGCCCCTGCTGGTCCTTGTTGCATGA
TCTTGACACATTTGGCCTCTTTTCGCAGCCTCCCGCTGTGGGCTGTGGCGATCCTCACCCTCTTCCTTGATATCGACGGG
ATCGGCACACTCACCTGGGTTTCTTTCATCCCTCTCATCATCCTCTTGTGTGTTGGAACCAAGCTAGAGATGATCATCAT
GGAGATGGCCCTGGAGATCCAGGACCGGTCGAGCGTCATCAAGGGGGCACCCGTGGTCGAGCCCAGCAACAAGTTCTTCT
GGTTCCACCGCCCCGACTGGGTCCTCTTCTTCATACACCTGACGCTGTTCCAGAACGCGTTTCAGATGGCACATTTCGTG
TGGACAGGCATGCGACTGG
```

Figure 9a characteristics of pWIR5-TaMlo-RNAi:

| | |
|---|---|
| total length | 7633 bp |
| vector Backbone: pBluescript | SK+, entire construct between XhoI and SacI restriction sites |
| GstA1 promoter | 694-2891 |
| Transcription start: | 2892 |
| GstA1 5' UTR | 2892-2988 |
| WIR1 5' UTR (part) | 2989-3034 |
| WIR1 part of 5' CDS + Intron | 3035-3246 |
| TaMlo IR1 | 3252-3556 |
| Intron Mla1 | 3698-4731 |
| TaMlo IR2 | 4877-5190 |
| CamV 35S Terminator: | 5191-5391 |

Sequenz:
```
CTAAATTGTAAGCGTTAATATTTTGTTAAAATTCGCGTTAAATTTTTGTTAAATCAGCTCATTTTTTAACCAATAGGCCG
AAATCGGCAAAATCCCTTATAAATCAAAAGAATAGACCGAGATAGGGTTGAGTGTTGTTCCAGTTTGGAACAAGAGTCCA
CTATTAAAGAACGTGGACTCCAACGTCAAAGGGCGAAAAACCGTCTATCAGGGCGATGGCCCACTACGTGAACCATCACC
CTAATCAAGTTTTTTGGGGTCGAGGTGCCGTAAAGCACTAAATCGGAACCCTAAAGGGAGCCCCCGATTTAGAGCTTGAC
GGGGAAAGCCGGCGAACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCCATTCAGGCTGCG
CAACTGTTGGGAAGGGCGATCGGTGCGGGCCTCTTCGCTATTACGCCAGCTGGCGAAAGGGGGATGTGCTGCAAGGCGAT
TAAGTTGGGTAACGCCAGGGTTTTCCCAGTCACGACGTTGTAAAACGACGGCCAGTGAGCGCGCGTAATACGACTCACTA
TAGGGCGAATTGGGTACCGGGCCCCCCCTCGAGTCTAGAACTAGTGGATCCCCGACGCCGAAGTGGAGCCGACAGCCCCC
AGGTCCCAAGCCCTCGGCAGACTAGATCACTAGCCCTGGATCGGCGAGGTGACTGGATGACGAGCAGCACCTGGTCTGGC
GGGTGTTGGGCGAGTAGAACCAGGGGCGATGGCGACGCGCTGACCTTCTCCCCTCACCGGCGATCTGCTCCTTCTGGGTG
GGGGTCGCCGGCTGACGTTCTGTTGCGGGGTGGGGGTCGCCGGCTGGCGTTCTGCTGCGGGGTGGGAGTCGCCGACCGGC
GTGCTGCTGCTAGGACAATCGGTGAGGCCAGTTAGGTGCTAGCCGATCGATTGGCGAAGAGATCCGAGTCCTGGGGAGAT
CAGTGAGGCCAGGTGCTATTTGGCCTATCAATTGGCCAGGTTCTGGGAACGGGGCGTGGCGTGATCAACGAGGTGCTAGG
CTGCTAGCTAGGGAACTGGATCCTGGAACGTGGAGGAGGCAAGTCCGGTATGCTAAGTACTTTAACTTTCCTTCTTCACA
TCCACCTGATTCAGATTATTTTGATCTAAATTAACTTGCAAAAAATATATGTGTGATATCCATCTACTATAATTGCTTAC
AATCAAAATTATATGTGATTTTTTTTAGTTTAGAAGATTTATATGCACAGTAAATCTGAATGTTCTTCACATGCATGATT
TAGTTTAACTTTAAAGAGTTATACTAACTAGTCTTGATAAAGAGATCTTTTGGAGCAACACCAAACCTCGTGAGGTGTTT
TGCCTACGGAAAGGTTGTGCTATGTAATGATTATTATTAGGATCAAAGTTGTAGGATAAACGTAAAACCTTCTCGATGTA
TCTTTTATACAACATTGTAGTTTAGTTATATATGGAGAGAGTGATTTAACACTTTGTGTTTAAGAGTAGAATAAGTTATT
CCACACTCTAGCCAAACGAACTATTTGGCAAATATCTCGCTAGCTGGTGAGAGCCAGAGCCGTGGAAAGTCTGTCTTGCT
ATTAAGGCACAAGCATCAAACAGGAACATTTAGAGCCATGGAAAAGTGATGTGTCGCCTACCAATGGGCCAACTGCTAGC
GATGTAATAATAGCATCCAAGTTGATTTTTTATAGAACATGCAAGGCGTTGGCAAGTGGGAAAATGATTGATCGCTGGCA
AGCTTAACTCTCGGAACTTATAGCATTCAACTGAATCAGAACAAAGATTAAAAAAAAATACATTTCCATCGATAGTGAAA
AATTATTCAATTGAGTGACAACGAAAATCATATTGGAATGTACATTTACTTGTTGATTTTAAATTAGAGGCATTTTTCTA
CCTTTTTTAGTTAATAAGATATGCATATACCCACCCTTAGTGTTTTCGAGACAACGAGAGGGCACATTGCTTTTGGTGCT
ACCATCTCTCTCAAGCCTCAAATAAGTTGTGCGGACACGATTATCTTCCCGCGTTGGAATATCGTGGCCTGGTAGAGCTA
GCGAAAAATCTTCCATGTTGGAATATGTCGGCAGCCGGATAGCCGCCATGCATGTAAAGTCTCTTTTTACCTTTACACTTG
CTCAAGTGACACTGTATGTCGCCTACCACTTGCTAAATCAATGGGCCAACTGCTAGCGACGTAATAGTAGCAAGTTGATT
TACAGTGTTTTGCTACAGTTCTCTGACTTTGTTTCTTCATTTTAGACTAGCTGACTACTGTCGCTTACCTGCCTTCCCTT
CTCCACGTTAGAGGATCCAGTTCTGATATTGAGACCTCGACGATGGGAGGAAGGGCGCGATCGATGTGGAGTAATTTGAA
TTTCAAATCTATCTATCTGGGGTATATTGGTCCTTCACCGATGTTTGGGGGGCTGTCGGAAATTGGTTCCGCGATCTACA
AAAGTGAATGGAGGGAGTAGTTGTTTCTCCAATCCGTACCACGCACGTGTTTCTAACTAGTACTTACTTCCTTCGCACC
ACAATATGGAATAGAGGGAGTATCGATAAACTAACAAAGATGATTACTTACCCGGTTTAAATGATTCAAGAGCTCATTTA
ATTTGGCACTCATCATTTCATATATCTTTTTTGGTAGAAATGAAATAAAGCAGATCTAGACACTAGCTAAAAAGTCGATG
TAGCCTTGTTATTTCCTTGGGCCACGCGGGCCGGGTGTGGTGCTCCCTGCTCTGTGTATAAATGGAGATCAACATCCAAG
GCCTCCTCCCACACACACACGCTACAGAGCAGAGCAGAGTCTTGCTCCAGTATCTGCCCTCTCCTGCCTGCCTGTAGAGC
ATCCATCACGTGAAGTTCACGGACAAACTACGTACACAGGCAGCTAGCTCTCGAAACCTCGCTCGAAACGCACCTGCAGA
TCGCTCTCTTCGTCGTCGTCGCCGCGATCATCATCAACAGCTCCGTCTGCCTTGGAGCCACGGCCGTCCACGACGCCGCC
GCCTCAGGTCAGTCGTCGGACGGTGTCCGTTCATTTCCTCCCCATTTTTGTAATTGATTAACTTGTTTATACATGCTGACC
TCGACCTGCTGAATAACGTCCGTCCATGGTTTCCCGTCCAGGCACCCCGGGCCACTGTCCACACGAAATGTGCCATCTGA
AACGCGTTCTGGAACAGCGTCAGGTGTATGAAGAAGAGGACCCAGTCGGGGCGGTGGAACCAGAAGAACTTGTTGCTGGG
CTCGACCACGGGTGCCCCCTTGATGACGCTCGACCGGTCCTGGATCTCCAGGGCCATCTCCATGATGATCATCTCTAGCT
TGGTTCCAACACACAAGAGGATGATGAGAGGGATGAAAGAAACCCAGGTGAGTGTGCCGATCCCGTCGATATCAAGGAAG
AGGGTGAGGATCGCCACAGCCCACAGCGGGAGGCTGCGAAAAGAGGCCAAATGTGTCAAGATCATGCAACAAGGACCAGC
AGGGGCAAAGACCATGACGCAGCAAACTGATAGTATTTGTATCATATGGAAGCTAAGCAATATCATATGGAGCCTGACGAC
ACTCGTGCCGAATTCGATTCGTGAATTTCTAGAGAACAAAAGGTATGCATCAATTTAGAAAAAAGTACACTATTATGTGA
TGTTTGTTTCCTATGCTAGTGGAACGGATTAGAATTTTTTTTTCATTAAGGTCACCTTTACTGGCATAAGCAGTTCACAC
```

```
TAAACGGTAAACCTTATAGGTGAAAATTTTCAGGCATATATATATATATATATATATATATATGTTTGATTCTTTCCGGC
TTAACAAAATAATTAGCAAGTACTTCTTGTTGCATTTGTTCCAACGGCTGAATTTATTGGCATCGGTCAAGAAATCCAT
CTAAATGTTTTACATTTCACCAAAGTGTGTGTCATGACAGATGTAACAAATAATAAACCAAAAGGAGAGGAAGGAAAGAG
GAAGATAAATGTTACAAAAATTTAAATCAAACTTATTTCTACCTTTCTCCTTACCTACCCAGTTTAAAAACACATATTAT
ATTTTAAAGAGAGGCAACATGCGCCAAAGGCTACCCTTGAAAATTCCTAAAATATTGTACATTTGACTGATGACCAAACA
AAAAGTTAAATTGTCTCTTCCTTATCACATTATATTTCCATGCATGCCTTTTTCTGGAAACTTACTATCAGCAAAATTTA
GATGAAAGGATAATGCCACATAATTTCAGTCTCCAAGAGATTTGTTAGTTGTCATATATTAAATTGGTGGGCCAATCTAT
TCCTGGGTCTTTTTATGTATCTACTTGACCATTTGAACTTCTGTAGTTAATTGTATTCTATGAATGATCACTCATCCAAA
AACTTGTTATTTGTGTTTTACTCTGTTGAATCTTGAATATTTATTCATTTTGTTCATCATACGATTGGAGGCCCATAATA
GATGCTTAATGAGAGTAAGATTATCGATCTCCAAACACATGCTTCTTACTAGTGTTGAATATATACCCTTTTAGATGTAT
AGTTCAACCCATAGATTCATATGACCCTCAGCTTTCTGATGTGTATGTATGACCTTACACTGACACTCTGAACTAATGTA
GGTATCTTGTCCTGCAGGAATTCGGCACGAGTGTCGTCAGGCTCCATATGATATTGCTTAGCTTCCATATGATACAATAC
TATCAGTTTGCTGCGTCATGGTCTTTGCCCCTGCTGGTCCTTGTTGCATGATCTTGACACATTTGGCCTCTTTTCGCAGC
CTCCCGCTGTGGGCTGTGGCGATCCTCACCCTCTTCCTTGATATCGACGGGATCGGCACACTCACCTGGGTTTCTTTCAT
CCCTCTCATCATCCTCTTGTGTGTTGGAACCAAGCTAGAGATGATCATCATGGAGATGGCCCTGGAGATCCAGGACCGGT
CGAGCGTCATCAAGGGGGCACCCGTGGTCGAGCCCAGCAACAAGTTCTTCTGGTTCCACCGCCCGACTGGGTCCTCTTC
TTCATACACCTGACGCTGTTCCAGAACGCGTTTCAGATGGCACATTTCGTGTGGACAGGCATGCGACTGGGCATGCCCGC
TGAAATCACCAGTCTCTCTCTACAAATCTATCTCTCTCTATAATAATGTGTGAGTAGTTCCCAGATAAGGGAATTAGGGT
TCTTATAGGGTTTCGCTCATGTGTTGAGCATATAAGAAACCCTTAGTATGTATTTGTATTTGTAAAATACTTCTATCAAT
AAAATTTCTAATTCCTAAAACCAAAATCCAGGGGTACCGAGCTCGAATTCTAGTCTACGCGGCCGCGAGCTCCAGCTTTT
GTTCCCTTTAGTGAGGGTTAATTGCGCGCTTGGCGTAATCATGGTCATAGCTGTTTCCTGTGTGAAATTGTTATCCGCTC
ACAATTCCACACAACATACGAGCCGGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCTGCATTAATGAATCGGCCAACGCGCGGGGA
GAGGCGGTTTGCGTATTGGGCGCTCTTCCGCTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGATAACGCAGGAAAGAACATGTGAGCAAAAGG
CCAGCAAAAGGCCAGGAACCGTAAAAAGGCCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACGTTAAGGGATTTTGGTCATGAGATTATCAAA
AAGGATCTTCACCTAGATCCTTTTAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGTTCATCCATAGTTGCCTGACTCCCC
GTCGTGTAGATAACTACGATACGGGAGGGCTTACCATCTGGCCCCAGTGCTGCAATGATACCGCGAGACCCACGCTCACC
GGCTCCAGATTTATCAGCAATAAACCAGCCAGCCGGAAGGGCCGAGCGCAGAAGTGGTCCTGCAACTTTATCCGCCTCCA
TCCAGTCTATTAATTGTTGCCGGGAAGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTCCCAACGATCAAGGCGAGTTACATG
ATCCCCCATGTTGTGCAAAAAAGCGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGATGCTTTTCTGTGACTGGTGAGTAC
TCAACCAAGTCATTCTGAGAATAGTGTATGCGGCGACCGAGTTGCTCTTGCCCGGCGTCAATACGGGATAATACCGCGCC
ACATAGCAGAACTTTAAAAGTGCTCATCATTGGAAAACGTTCTTCGGGGCGAAAACTCTCAAGGATCTTACCGCTGTTGA
GATCCAGTTCGATGTAACCCACTCGTGCACCCAACTGATCTTCAGCATCTTTTACTTTCACCAGCGTTTCTGGGTGAGCA
AAAACAGGAAGGCAAAATGCCGCAAAAAAGGGAATAAGGGCGACACGGAAATGTTGAATACTCATACTCTTCCTTTTTCA
ATATTATTGAAGCATTTATCAGGGTTATTGTCTCATGAGCGGATACATATTTGAATGTATTTAGAAAAATAAACAAATAG
GGGTTCCGCGCACATTTCCCCGAAAAGTGCCAC
``` continuation figure 9a

Figure 11:
a)
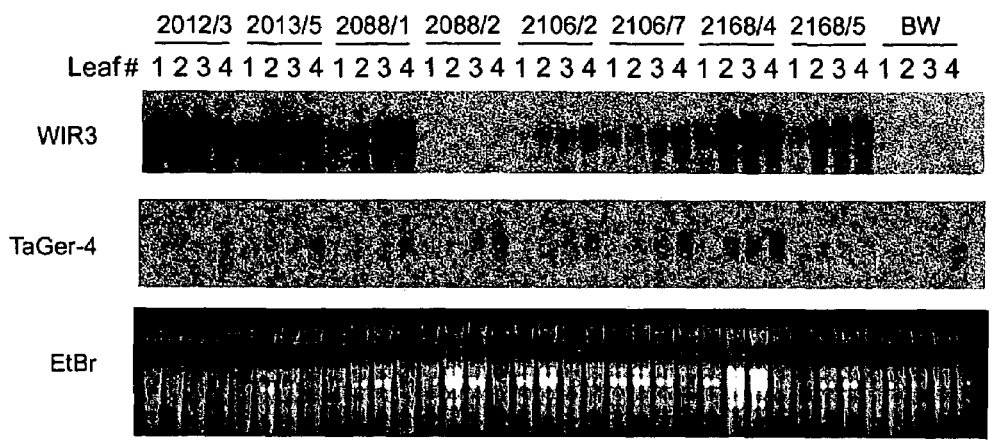
b)
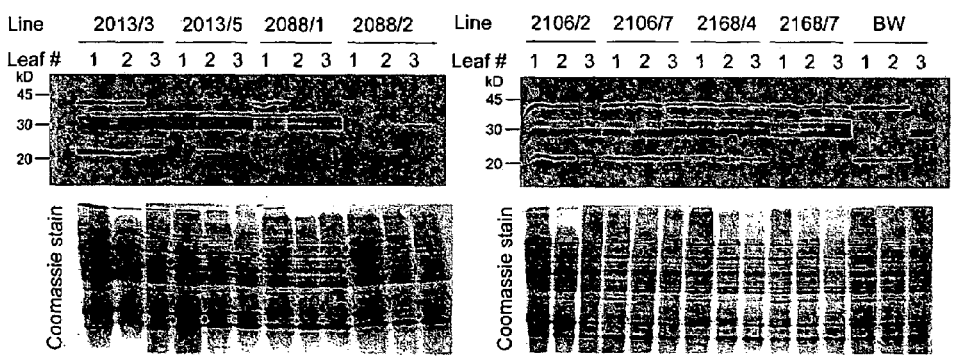

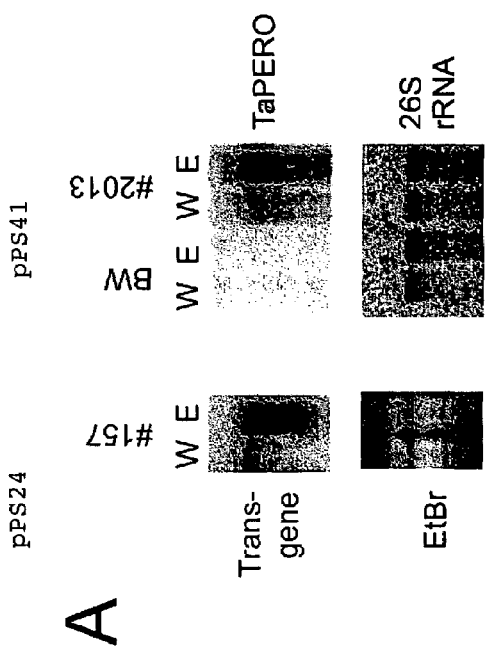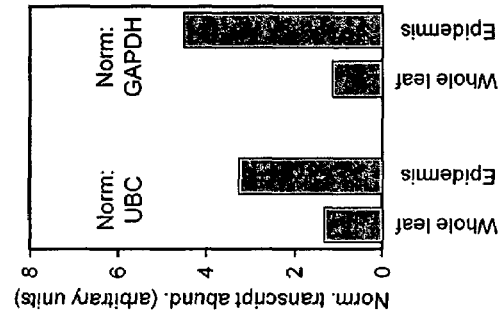
Figure 12

Figure 13:

Mildew resistance of transgenic wheat lines that carry the pPS41 construct.

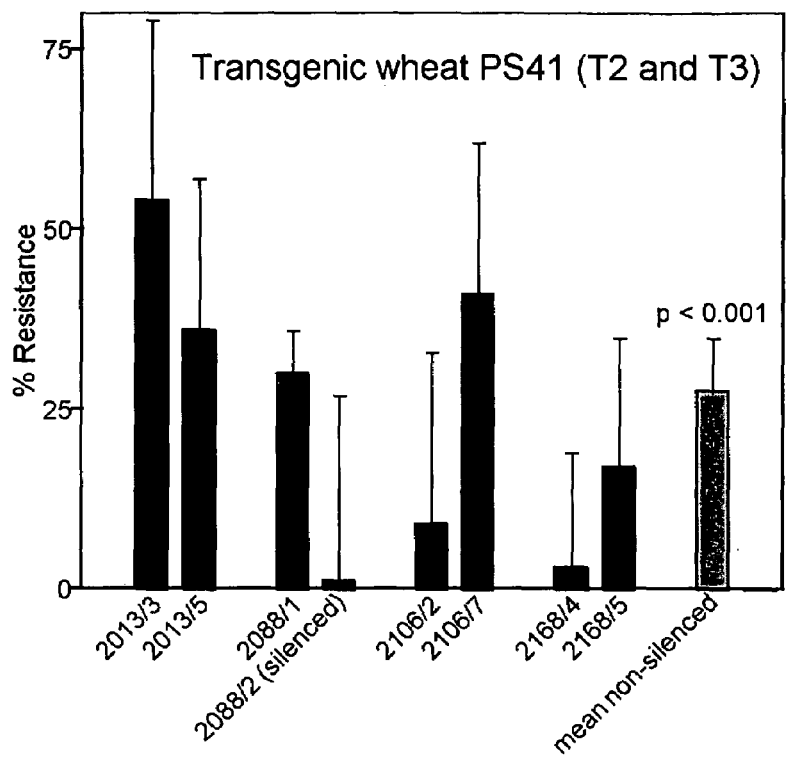

The flag leaf of adult plants was cut away and inoculated with wheat mildew in a detached leaf assay together with Bobwhite wild-type plants. 7 days after inoculation, the mildew infection was evaluated. Mean values from 3 independent inoculation experiments with plants of the T2 and T3 generation are shown. Subline 2088/2 does not express TAPERO and is not increased resistant. Mean non-silenced = mean value of all lines except 2088/2 and all experiments.

Normal growth-phenotype of transgenic plants carrying the pPS41 construct.

Plants of the T2 generation were sown together with Bobwhite wild-type plants and photographed in the adult plant stage.

Mildew resistance of transgenic wheat lines carrying the pWIR5-TaMlo-RNAi construct.

The flag leaf of adult plants of the T2 generation was cut away and inoculated with wheat mildew in a detached leaf assay together with Bobwhite wild-type plants. 7 days after inoculation, the mildew infection was evaluated. 2 sublines per line were tested in each case.

PROMOTERS FOR EPIDERMIS-SPECIFIC EXPRESSION OF DESIRED CODING SEQUENCES IN TRANSGENIC PLANTS

CROSS-REFERENCE TO RELATED APPLICATIONS

This application is the National Stage application under 35 U.S.C. §371 of PCT Application No. PCT/EP/2004/011214, filed Oct. 7, 2004, and published on Apr. 21, 2005 as WO 2005/035766, which claims priority to German Application No. 103 46 611.8, filed Oct. 7, 2003.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to promoter regions, under whose control transgenes can be epidermis-specifically expressed in plants. Furthermore, the invention relates to recombinant nucleic acid molecules, which comprise said promoter regions, and to transgenic plants and plant cells, which have been transformed by means of said nucleic acid molecules, as well as to methods for their generation. Furthermore, the present invention relates to nucleic acid molecules comprising a promoter according to the present invention, and to nucleic acid sequences or transgenes, which are capable of mediating pathogen resistance, as well as to plants and plant cells transformed by means of said nucleic acid molecules, and to methods for their generation.

2. Description of Related Art

Those DNA regions of a gene, which are located upstream of the transcription initiation point and by which the initiation point and the initiation frequency of the transcription and thus the expression level and the expression pattern of the controlled gene are determined, are in general referred to as promoters. RNA polymerase and specific transcription factors activating the RNA polymerase bind to the promoters in order to initiate transcription together with the basal transcription complex. The effectiveness of the promoters is often enhanced and regulated by additional DNA sequences, the enhancer sequences, whose position, contrarily to the position of the promoters, is not fixed. These regulatory elements can be located upstream, downstream, or in an intron of the gene to be expressed.

In recombinant DNA technology, promoters are inserted into expression vectors in order to control the expression of a transgene, which is normally not the gene naturally regulated by the promoter. Of substantial significance herein is the specificity of the promoter, which determines at which point in time, in which types of tissue, and at which intensity a gene transferred by means of genetic engineering is expressed.

In plant breeding, recombinant DNA technology is often used for transferring specific advantageous properties to useful plants, which is supposed to lead to a higher yield, for example by means of increased pathogen resistance, or to improved properties of the harvest products. Herein, it is often desirable that the transferred gene be not expressed ubiquitously, but only in those tissues, where the transgenic activity is desired, as the presence of the transgenic product can have a negative effect on normal physiological processes in some tissues. Thus, it could, for example, be shown that the overexpression of an anionic peroxidase under the control of the ubiquitously effective 35S promoter leads to wilting of transgenic tobacco plants, as less root growth occurs and therefore also less root mass is developed (Lagrimini et al. (1997) The consequence of peroxidase overexpression in transgenic plants on root growth and development. Plant Mol Biol. 33 (5), S. 887-895). The overexpression of the spi2 peroxidase under the control of the likewise ubiquitously effective ubiquitin promoter, leads to reduced epicotyl development and reduced longitudinal growth in comparison with control plants (Elfstrand, M. et al. (2001) Overexpression of the endogenous peroxidase-like gene spi2 in transgenic Norway spruce plants results in increased total peroxidase activity and reduced growth. Plant Cell Reports 20 (7), S. 596-603). Irrespective of negative effects on physiological processes, it is often supposed to be prevented in resistance breeding that the transgenic product is also present in the harvested plant parts.

Therefore, promoters functioning either tissue-specifically or inducibly have been isolated during the past years. Tissue-specific promoters are, for example, seed-, tuber-, and fruit-specific promoters. The inducible promoters can be activated, for example, by means of chemical induction, light induction, or other stimuli.

BRIEF SUMMARY OF THE INVENTION

It is also desirable to specifically modulate gene expression in the epidermis. The epidermis is the terminal tissue of the above-ground organs of higher plants. As such, the tasks of the epidermis are, on the one hand, to allow water and nutrient exchange of the plant and, on the other hand, to prevent the intrusion of pathogens into the plant. These functions could be specifically modulated by means of altered gene expression in the epidermis with the aid of suitable promoters and genes controlled by the latter.

Epidermis-specific promoters have already been described in dicotyledonous plants. It could thus be shown that the promoter of the CER6- (CUT1-) gene from *Arabidopsis*, which codes for a condensing enzyme in wax synthesis, can cause the epidermis-specific expression of a β-glucuronidase reporter gene (Hooker et al. (2002), Significance of the expression of the CER6 condensing enzyme for cuticular wax production in *Arabidopsis*, Plant Physiol. 129(4), S. 1568-1580; Kunst et al. (2000), Expression of the wax-specific condensing enzyme CUT1 in *Arabidopsis*, Biochem. Soc. Trans. 28(6), S. 651-654).

However, suitable epidermis-specific promoters in monocotyledonous plants, which are particularly well suitable for the expression of transgenes in monocotyledons, in particular in poaceae (sweet grasses), could not successfully be identified up to now. Therefore, constitutive promoters like the ubiquitin promoter from maize were hitherto used in order to express proteins in the epidermis (see, for example, Oldach et al. (2001), Heterologous expression of genes mediating enhanced fungal resistance in transgenic wheat, Mol Plant Microbe Interact. 14(7), S. 832-838). However, this can lead to undesired side effects in the transgenic plants due to the presence of the transgenic product in other tissues or organs than the epidermis, as is described above.

It is therefore the problem underlying the present invention to provide means allowing an epidermis-specific gene expression in monocotyledons, preferably in cereal plants.

This problem is solved by provision of the embodiments characterized in the patent claims.

Thus, the present invention relates to a promoter region having specificity for the plant epidermis, comprising a first sequence originating from the promoter of the gene glutathione-S-transferase A1 (GSTA1) and a second sequence originating from the intron of the gene WIR1a. GSTA1 relates to genes as they are described in Dudler et al. (1991), A pathogen-induced wheat gene encodes a protein homologous to glutathione-S-transferases, Mol. Plant Microbe Interact. 4(1), S. 14-18. In particular, these genes are genes from wheat; they can, however, also be homologous genes from other cereal plants, in particular from barley, having a comparable expression pattern and a similar-gene product. WIR1a denotes genes as they are described in Bull et al. (1992), Sequence and expression of a wheat gene that encodes a novel protein associated with pathogen defense, Mol. Plant Microbe Interact. 5(6), S. 516-519.

Preferably, the first sequence is SEQ ID No. 1 and the second sequence is SEQ ID No. 2.

Between the first and the second sequence there can be further non-translated sequences having a length of 10 bp to 1000 bp, preferably of 20 bp to 800 bp, particularly preferably of 30 bp to 500 bp, and most preferably between 40 bp and 300 bp.

Particularly preferably, the promoter region according to the present invention is a promoter region selected from the group consisting of
 a) promoter regions comprising the nucleic acid sequence given in SEQ ID No. 3;
 b) promoter regions comprising a functional part of the nucleic acid sequence given in SEQ ID No. 3 or
 c) promoter regions having a sequence, which hybridizes under stringent conditions with the nucleic acid sequence given in SEQ ID No. 3.

DETAILED DESCRIPTION OF THE INVENTION

Within the scope of the present invention, a promoter region is understood to be a nucleic acid sequence comprising the regulatory sequences required for the expression of a coding sequence (transgene). Regulatory sequences form that part of a gene, which determines the expression of a coding sequence, i.e. in particular the expression level and pattern. The regulatory sequences have at least one sequence motif, where the specific transcription factors and the RNA polymerase bind, assemble to form the transcription complex, and effectively initiate the transcription of the nucleic acid sequence controlled by the promoter region.

The promoter regions according to the present invention are based on the observation that promoters having new properties can be generated by means of fusing the promoter of the GSTA1 gene from wheat with intron sequences of the WIR1a gene from wheat.

In transient reporter gene assays in wheat leaves having a β-glucuronidase (GUS) gene from *E. coli* as reporter gene, different combinations of the WIR1a promoter and intron and the GST promoter were tested. Surprisingly, it showed that GST promoter and WIR1a intron have a synergistic effect on reporter gene activity. The increase in transcriptional activity was comparable to the transcriptional activity achieved by means of the ubiquitously expressed 35S promoter.

Within the scope of the present invention, the term "epidermis-specific" is understood to denote that a nucleic acid sequence, which is under the control of the promoter region according to the present invention, is expressed in the shoot epidermis of plants. In the sense of the present invention, epidermis-specificity is, in particular, also given, if the promoter region according to the present invention favors the expression of a foreign gene in the epidermis in comparison with other cell types and causes a significantly increased, like at least double, preferably at least 5-fold, particularly preferably at least 10-fold, and most preferably at least 50-fold, expression in comparison with other cell types. The expression level can be determined by means of conventional in situ detection techniques.

The term "plant epidermis" is known to the person skilled in the art. Complementary information can be found in any book on plant anatomy or plant physiology, like, for example, in Strasburger, Lehrbuch der Botanik, 35. edition 2002, Spektrum Akademischer Verlag.

It has now surprisingly be found, that a promoter region, which comprises both regulatory sequences from the GSTA1 gene from wheat and intron sequences from the WIR1a gene from wheat, causes epidermis-specific expression of a coding nucleic acid sequence, which is under its control.

Beside a promoter region having the nucleic acid sequences depicted in SEQ ID No. 3, the present invention also relates to promoter regions having functional parts of said sequence and causing epidermis-specific expression of one of the coding nucleic acid sequences, which they control, in plants.

In this context, a "functional part" is understood to denote sequences, which the transcription complex, despite a slightly deviating nucleic acid sequence, can still bind to and cause epidermis-specific expression. Functional parts of a promoter sequence also comprise such promoter variants, whose promoter activity is lessened or enhanced in comparison with the wild-type. In particular, a functional part is, of course, also understood to denote natural or artificial variants of the sequence of the promoter region given in SEQ ID No. 3. Mutations comprise substitutions, additions, deletions, exchanges, and/or insertions of one or more nucleotide residue/s. Within the scope of the present invention, functional parts of the promoter regions comprise naturally occurring variants of SEQ ID No. 3 as well as artificial nucleotide sequences, for example obtained by means of chemical synthesis.

In any case, the promoter used contains a TATA box (positions 2163 to 2169 in SEQ ID Nos. 1 and 3) and preferably also two CAAT boxes (positions 1047 to 1051 or 1895 to 1899 in SEQ ID Nos. 1 and 3). Furthermore, the promoter contains at least one, preferably at least two and three, particularly preferably at least four, five, and six, and most preferably at least seven or eight of the following sequence motifs:

| | |
|---|---|
| a) | GTGGGGG |
| b) | ACGTGGA |
| c) | TCCACCT |
| d) | TATCCAT |
| e) | CATGCATG |
| f) | TGTAAAG |
| g) | CCTACCA |
| h) | AATAGTA |

Preferably, the sequence motifs are located at the positions corresponding to the following positions in SEQ ID Nos. 1 and 3:
a) 185-191 and 217-223 bp
b) 455-461 bp
c) 508-514 bp
d) 564-570 bp
e) 1514-1521 bp
f) 1520-1526 bp
g) 1569-1575 bp
h) 1610-1616 bp The promoter activity of variants of the promoter region can be measured with the aid of marker genes, whose coding sequence is under the control of the promoter region to be examined. Suitable marker genes are, for example, the β-glucuronidase (GUS) gene from *E. coli*, a fluorescence gene like, for example, the green fluorescence protein (GFP) gene from *Aequoria victoria*, the luciferase gene from *Photinus pyralis* or the β-galactosidase (lacZ) gene from *E. coli*. Absolute promoter activity is determined by means of comparison with a wild-type plant. Tissue or cell specificity can easily be determined by means of comparison of the expression rates of the above-mentioned marker genes in the respective tissues or cells.

The present invention also relates to promoter regions having a nucleic acid sequence hybridizing with the nucleic acid sequence given in SEQ ID No. 3 under stringent conditions. In the context of the present invention, the term "hybridization under stringent conditions" means that hybridization is conducted in vitro under conditions, which are stringent enough to ensure a specific hybridization. Such stringent hybridization conditions are known to the person skilled in the art and can be taken from the literature (Sambrook et al. (2001), Molecular Cloning: A Laboratory Manual, 3. edition, Cold Spring Harbor Laboratory Press, Cold Spring Harbor, N.Y.).

In general, "specifically hybridize" means that a molecule preferentially binds to a specific nucleotide sequence under stringent conditions, if said sequence is present in the form of a complex mixture of (for example total) DNA or RNA. The term "stringent conditions" generally denotes conditions, under which a nucleic acid sequence will preferentially bind to its target sequence and to a considerably smaller extent or not at all to other sequences. Stringent conditions are partially sequence-dependent and will be different under different circumstances. Longer sequences specifically hybridize at higher temperatures. In general, stringent conditions are selected in such a way that the temperature lies about 5° C. below the thermal melting point ($T_m$) for the specific sequence at a defined constant ionic strength and a defined pH value. $T_m$ is the temperature (under defined ionic strength, pH value, and nucleic acid concentration), at which 50% of the molecules complementary to the target sequence hybridize to the target sequence in a state of equilibrium. Typically, stringent conditions are those, wherein the salt concentration is at least about 0.01 to 1.0 M sodium ion concentration (or any other salt) at a pH value of between 7.0 and 8.3 and the temperature is at least 30° C. for short molecules (i.e. for example 10 to 50 nucleotides). In addition, stringent conditions can be achieved by means of adding destabilizing agents, like for example formamide.

Suitable stringent hybridization conditions are, for example, also described in Sambrook et al., vide supra. Thus, hybridization can, for example, occur under the following conditions:
hybridization buffer: 2×SSC, 10× Denhardt's solution (Fikoll 400+PEG+BSA; ratio 1:1:1), 0.1% SDS, 5 mM EDTA, 50 mM $Na_2HPO_4$, 250 μg/ml herring sperm DNA; 50 μg/ml tRNA or 0.25 M sodium phosphate buffer pH 7.2, 1 mM EDTA, 7% SDS at a hybridization temperature of 65° C. to 68° C.
washing buffer: 0.2×SSC, 0.1% SDS at a washing temperature of 65° C. to 68° C.

Preferably, such promoter variants have a sequence identity of at least 50%, preferably at least 70%, particularly preferably at least 90%, and most preferably at least 95% to the promoter sequence given in SEQ ID No. 3 or parts thereof, in relation to the total DNA sequence shown in SEQ ID No. 3. Preferably, the sequence identity of such promoter sequences is determined by means of comparison with the nucleic acid sequence given under SEQ ID No. 3. In case two nucleic acid sequences of different length are compared to each other, the sequence identity preferably relates to the percentage of the nucleotide residues of the shorter sequence, which are identical to the corresponding nucleotide residues of the longer sequence.

Sequence identities are conventionally determined via different alignment programs, like for example CLUSTAL. In general, the person skilled in the art has at his disposal suitable algorithms for determining the sequence identity.

The percentage degrees of identity given above for SEQ ID No. 3 also apply to the first and second sequences of the promoter region according to the present invention, which are shown in SEQ ID Nos. 1 and 2.

In a preferred embodiment of the invention, the promoter region according to the present invention has the total sequence of 2552 nucleotides, which is given under SEQ ID No. 3.

The present invention also relates to chimeric genes of the promoter-region according to the present invention and of a coding sequence, whose expression, which is naturally not regulated by the promoter region according to the present invention, in the chimeric gene is regulated by the promoter region according to the present invention, in operative linkage as well as to recombinant nucleic acid molecules containing said chimeric gene.

The term "nucleic acid sequence, whose expression is regulated by the promoter region according to the present invention" means that the expression of the nucleic acid sequence under the control of the promoter region according to the present invention in those cells, in which the promoter region is active, can be increased by at least the factor five, preferably at least the factor 10, and particularly preferably at least the factor 50 in comparison with the wild-type cells.

The nucleic acid sequence, whose expression is regulated by the nucleic acid sequence according to the present invention, can be the coding region of a transgene, for example a resistance gene, whose gene product is desired in the epidermis. By means of expression of the transgene, the content of the gene product encoded by it can be increased by at least the factor 2, preferably by at least the factor 5, particularly preferably by at least the factor 10, and most preferably by at least the factor 50.

However, the promoter region according to the present invention can also be used in RNAi constructs for RNA interference in order to achieve the epidermis-specific silencing of specific genes, whose gene products are supposed to be present in the epidermis to a smaller extent than usual or not at all. Of course, the latter can also be achieved by means of classic antisense or co-suppression constructs with the use of the promoter region according to the present invention. By means of the silencing constructs, the expression of the endogenous gene is decreased by at least 50%, preferably by at least 70%, particularly preferably by at least 90%, and particularly preferably by at least 95%.

In a construct, which is supposed to be used for RNA interference, there are usually palindromic DNA sequences, which form double-stranded RNA subsequent to the transcription. By means of the dicer enzyme, said double-stranded RNA is processed to form shorter RNA pieces, which bind to an endogenous RNA and cause its degradation with the aid of the RISC (RNA-induced silencing complex) (Hannon (2002) RNA Interference, Nature, Bd. 418, S. 244-251).

The effect of the gene silencing constructs on the expression of the endogenous gene can be detected by means of conventional molecular biological methods, which are well known to the person skilled in the art. Thus, Northern blot and RT-PCR methods are available for examining the RNA level; the protein can be detected by means of Western blot analyses, immunofluorescences, or, provided that the protein is an enzyme, by means of enzyme assays.

Within the scope of the present invention, the term "transgene" summarizes those genes, whose gene products are supposed to be provided in the epidermis or are supposed to be suppressed in gene silencing.

Preferably, the nucleic acid sequence, whose expression is under the control of the promoter according to the present invention, is a nucleic acid sequence, which mediates pathogen resistance, as the epidermis is the first band, which has to be surmounted by a pathogen when intruding into the plant.

Within the scope of the present invention, the term "recombinant nucleic acid molecule" is understood to denote a vector, which contains a chimeric gene according to the present invention or a promoter region according to the present invention and which can cause the promoter-dependent expression of the nucleic acid sequence, which is under the control of the promoter region according to the present invention, in plant cells and plants. In a preferred embodiment, a recombinant nucleic acid molecule according to the present invention additionally contains transcription termination sequences. Herein, "transcription termination sequences" are understood to denote DNA sequences, which are located at the downstream end of a coding sequence and which cause the RNA polymerase to terminate the transcription.

Furthermore, the invention relates to methods for generating transgenic plants with epidermis-specific expression of a nucleic acid sequence, which is regulated by the promoter region according to the present invention, comprising the following steps:
a) generating a recombinant nucleic acid molecule, in which the promoter region according to the present invention is present in operative linkage with a coding sequence,
b) transferring the nucleic acid molecule from a) to plant cells and
c) regenerating entirely transformed plants and, if desired, propagating the plants.

For the preparation of the introduction of foreign genes into higher plants and their cells, respectively, a large number of cloning vectors containing a replication signal for *E. coli* and a marker gene for selecting transformed bacteria cells are available. Examples for such vectors are pBR322, pUC series, M13mp series, pACYC184, and so on. The chimeric gene can be introduced into the vector at a suitable restriction site.

The plasmid obtained is then used for transforming *E. coli* cells. Transformed *E. coli* cells are cultivated in a suitable medium and are subsequently harvested and lysed and the plasmid is re-obtained. Restriction analyses, gel electrophoreses, and further biochemical-molecular biological methods are generally used as analysis methods for characterizing the obtained plasmid DNA. Subsequent to each manipulation, the plasmid DNA can be cleaved and DNA fragments obtained therefrom can be linked with other DNA sequences.

As already mentioned, a variety of techniques for introducing DNA into a plant host cell are available, wherein the person skilled in the art can determine the method suitable in each case without any difficulties. Said techniques comprise transformation of plant cells with T-DNA using *Agrobacterium tumefaciens* or *Agrobacterium rhizogenes* as transformation medium, fusion of protoplasts, injection, electroporation, direct gene transfer of isolated DNA into protoplasts, introduction of DNA by means of biolistic methods as well as further possibilities, which are well established for several years now and which belong to the standard repertoire of the person skilled in the art of plant molecular biology and plant biotechnology, respectively. The biolistic gene transfer method is, in particular, used in monocotyledonous plants. Here, the person skilled in the art can find useful information on the conduction, like for example in Vasil et al. (1992) Bio/Technology, 10, S. 667-674; Vasil et al. (1993) Bio/Technology, 11, S. 1153-1158; Nehra et al. (1994) Plant J. 5, S. 285-297; Becker et al. (1994) Plant J., 5, S. 299-307; Altpeter et al. (1996) Plant Cell Reports 16, S. 12-17; Ortiz et al. (1996) Plant Cell Reports 15, S. 877-81; Rasco-Gaunt et al. (2001) J. Exp. Bot. 52; S. 865-874.

In the case of injection and electroporation of DNA into plant cells, no specific demands per se are made on the plasmids used. This also applies to direct gene transfer. Simple plasmids, like for example pUC derivatives, can be used.

However, if whole plants are supposed to be regenerated from cells transformed in this manner, the presence of a selectable marker gene is recommendable. Standard selection markers are known to the person skilled in the art and selecting a suitable marker does not pose a problem.

According to the method of introducing the desired genes into the plant cell, further DNA sequences can be required. If, for example, the Ti or Ri plasmid is used for transforming the plant cell, at least the right border, though often the right and left border, of the T-DNA contained in the Ti or Ri plasmid, have to be joined with the genes, which are supposed to be introduced, to form a flanking region. If agrobacteria are used for transformation, the DNA, which is supposed to be introduced, has to be cloned into specific plasmids, actually either into an intermediate or into a binary vector. Due to sequences, which are homologous to sequences in the T-DNA, the intermediate vectors can be integrated into the Ti or Ri plasmid of the agrobacteria by means of homologous recombination. Said plasmid also contains the vir region necessary for the transfer of the T-DNA. However, intermediate vectors cannot replicate in agrobacteria. By means of a helper plasmid, the intermediate vector can be transferred to *Agrobacterium tumefaciens* (conjugation). Binary vectors, however, can replicate in both *E. coli* and in agrobacteria. They contain a selection marker gene and a linker or polylinker, which are framed by the right and left T-DNA border region. They can be transformed directly into the agrobacteria. The *agrobacterium* serving as a host cell should contain a plasmid carrying the chimeric gene within the T-DNA, which is transferred into the plant cell. Additional T-DNA can be present. The *agrobacterium* transformed in such a way is used for the transformation of plant cells. The use of T-DNA for the transformation of plant cells has been intensely examined and sufficiently described in commonly known survey articles and manuals on plant transformation. In the case of monocotyledonous plants, altered protocols must be applied for effective *agrobacterium*-mediated gene transfer, as they are, for example, described in Cheng et al. (1997) Plant Physiol. 115, S. 971-980; Khanna and Daggard (2003) Plant Cell Reports 21, S. 429-436; Wu et al. (2003) Plant Cell Reports 21, S. 659-668; Hu et al. (2003) Plant Cell Reports 21, S. 1010-1019. For the transfer of the DNA into the plant cell, plant explants can advisably be cultivated with *Agrobacterium tumefaciens* or *Agrobacterium rhizogenes*. Whole plants can then be regenerated from the infected plant material (e.g. pieces of leaves, segments of stems, roots, but also protoplasts or suspension-cultivated plant cells) in a suitable medium, which can contain antibiotics or biocides for the selection of transformed cells.

Once the introduced DNA is integrated in the genome of the plant cell, it is normally stable there and is also maintained in the offspring of the originally transformed cell. The introduced DNA normally contains a selection marker, which mediates resistance against a biocide or an antibiotic like kanamycin, G 418, bleomycin, hygromycin, methotrexate, glyphosate, streptomycin, sulfonylurea, gentamycin or phosphinotricin and others to the transformed plant cells. The individually selected marker should therefore allow the selection of transformed cells against cells lacking the introduced DNA. To this end, alternative markers, like nutritive markers or screening markers (like GFP, green fluorescent protein), are also suitable. Selection markers can, of course, also be entirely omitted, which, however, is accompanied by a comparatively high screening necessity. In case marker-free transgenic plants are desired, the person skilled in the art has also at his disposal strategies, which allow removing the marker gene later on, for example co-transformation or sequence-specific recombinases.

Regeneration of the transgenic plants from transgenic plant cells is conducted according to conventional regeneration methods using known nutritive media. The plants obtained in this manner can then be examined by means of conventional methods, including molecular biological methods like PCR, blot analyses for presence and tissue specificity of the introduced nucleic acid sequence, whose expression is controlled by the promoter according to the present invention, or for endogenous RNAs and proteins influenced by said nucleic acid sequence.

Furthermore, the invention relates to transgenic plants containing a nucleic acid sequence regulated by the promoter region according to the present invention and epidermis-specifically expressing said nucleic acid sequence.

Preferably, the plants according to the present invention are monocotyledons, in particular cereal plants like rye, maize, and oats, particularly preferably wheat or barley, as well as transgenic parts of said plants and their transgenic propagation material, like protoplasts, plant cells, calli, seeds, tubers or cuttings, as well as the transgenic offspring of said plants. However, the promoter region according to the present invention can also be used in other poaceae (sweet grasses), like for example feed grasses, for generating corresponding plants having epidermis-specific expression of transgenes.

Genes for the production of epicuticular waxes can also be expressed under the control of the epidermis-specific promoter according to the present invention in order to increase drought tolerance of the plants. In addition, genes for the production of anthocyanins or other UV-absorbing substances for increasing UV-resistance can also be expressed under the control of the promoter according to the present invention. As was already worked out in the above, pathogen resistance genes are preferably expressed under the control of the promoter according to the present invention.

Bacteria, viruses, and fungi, which infect plants and thereby negatively influence the metabolism of the plant, are, inter alia, referred to as plant pathogens.

Among these plant pathogens are fungi, which, inter alia, cause the diseases mildew and stem break in cereal plants like wheat and barley. Depending on the degree of infection, these diseases can cause considerable yield losses (up to 50%).

Traditionally, the above-mentioned and further fungal plant diseases are controlled by means of fungicides, which have the known disadvantages, like percolation into groundwater and accumulation in the food chain.

Over the last few years, however, several genes, which are capable of mediating resistance against a specific agent or against several agents, were identified. The term "mediation of pathogen resistance", as it is used herein, means that plants, in which the expression of said genes is increased, are less susceptible for infections with specific pathogens in comparison with plants, in which the expression of said genes is normal. Among the genes, which mediate pathogen resistance, are also such genes, whose expression is activated by infection with a pathogen.

Among these genes are peroxidases and oxalate oxidases. The oxalate oxidases, which belong to the family of the germin-like proteins, catalyze the oxidation of oxalate, whereby hydrogen peroxide is formed. Hydrogen peroxide acts microbicidally and can enhance the lignification of the cell walls, whereby the intrusion of pests is prevented. Moreover, it can cause hypersensitive cell death at low concentrations. The peroxidases use either molecular oxygen or hydrogen peroxide in order to oxidize and thereby detoxify cellular substrates.

Pathogens, against which the expression of the oxalate oxidases and peroxidases in the epidermis of plants can mediate resistance, for example comprise: mildew, *fusarium* spp., *rynchosporium secalis* and *pyrenophora teres*. Further genes, which are capable of mediating resistance against pathogens, are chitinases, Ag-AFP, GSTA1, and WIR1a.

By means of expressing the nucleic acid sequence coding for said enzymes in the epidermis of transgenic plants with the aid of the promoter region according to the present invention, plants having increased pathogen resistance can be obtained.

In contrast to the genes mediating pathogen resistance, there are also plant-inherent genes, which promote the intrusion of a pathogen. Among those is the Mlo gene, which codes for a seven transmembrane receptor, which seems to promote the intrusion of the mildew fungus into the epidermis. In this case, it is appropriate to interfere with the expression of the Mlo gene in order to prevent the intrusion of fungi into the plant. This can, for example, be conducted with the aid of the above-described RNAi method. The fact that the interference with the expression of the Mlo gene is suitable for preventing the intrusion of the mildew fungus into the plant was shown in vitro in leaf segments from barley, which were bombarded with tungsten particles, which had been coated with Mlo-dsRNA (Schweizer et al. (2000), Double-stranded RNA interferes with gene function at the single-cell level in cereals, The Plant Journal, 24 (6), S. 895-903). However, it could hitherto not be shown that the epidermis-specific interference with the Mlo expression in transgenic plants has the same effect.

Further plant genes, which mediate the interaction of a pathogen with the plant and can thereby promote the intrusion of the pathogen into the plant, are, for example, amino acid or sugar transporters or invertases. Said genes are also suitable as targets for gene silencing. Thus, the present invention relates to methods for generating pathogen-resistant plants, comprising the steps:
a) generating a recombinant nucleic acid molecule, in which the promoter according to the present invention is present in operative linkage with a nucleic acid sequence mediating pathogen resistance,
b) transfer of the recombinant nucleic acid molecule from a) to plant cells and
c) regenerating entirely transformed plants and, if desired, propagating said plants.

Preferably, the nucleic acid sequence mediating pathogen resistance is the coding region of a peroxidase or oxalate oxidase gene or a sequence, which interferes with the endogenous Mlo-RNA.

The following Examples serve for illustrating the invention and are not supposed to be understood as limiting.

BRIEF DESCRIPTION OF THE DRAWINGS

Figures:
1) nucleic acid sequence of the GSTA1 promoter (SEQ ID No. 1)
2) nucleic acid sequence of the WIR1a intron (SEQ ID No. 2)
3) nucleic acid sequence of the preferred promoter region (SEQ ID No. 3)
4) nucleic acid sequence of the TAPERO (peroxidase) cDNA (SEQ ID No. 4)
5) TAPERO expression vector pPS41
  a) nucleic acid sequence (SEQ ID No. 5)
  b) vector map
6) nucleic acid sequence of the germin 9f-2.8 (oxalate oxidase) cDNA (SEQ ID No. 6)
7) germin expression vector pPS24
  a) nucleic acid sequence (SEQ ID No. 7)
  b) vector map
8) sequence of the Mlo-RNAi construct (SEQ ID No. 8)
9) Mlo-RNAi expression vector pWIR5-TaMlo RNAi
  a) nucleic acid sequence (SEQ ID No. 9)
  b) vector map
10) In situ oxalate oxidase activity in pPS24 transgenic plants
  Leaves from Bobwhite wild-type plants (BW) and from transgenic lines No. 157 and No. 170 were crosscut and the oxalate oxidase activity was detected in situ. Left column=reaction with oxalate substrate; right column=control reaction without oxalate substrate. The intense violet coloring indicates oxalate oxidase activity in the epidermis of the transgenic lines.
11) Detection of the TAPERO transgene in pPS41 transgenic plants
  a) in the Northern blot
  Detection of the accumulation of TAPERO RNA by means of hybridization of a WIR3 sample to Northern blots from transgenic wheat lines of the T2 generation, which carry the pPS41 construct. In each case, 2 sublines of 4 selected lines plus wild-type (BW) were analyzed in the adult plant stage. Leaf 1=flag leaf. Leaves 2 to 4=increasingly older. The TaGer-4 probe hybridizes to a group of stress-induced wheat genes and was used for testing pleiotropic side effects of the TAPERO overexpression. No significant side effect was found. EtBr=Loading control of the gels, stained with ethidium bromide.
  b) in the Western blot
  Detection of the accumulation of the TAPERO protein by means of antibody reaction on Western blots of transgenic wheat lines of the T2 generation, which carry the pPS41 construct. The TAPERO transgenic product has the expected size of 31 kD. In Bobwhite, leaf 3, an increased basal activity of the TAPERO gene can be observed: Leaf 1=flag leaf. Coomassie stain=loading control of the gels, stained with Coomassie blue R 250.
12) Detection of the epidermis-specific transgenic expression
  A) by means of Northern blot analysis
  Detection of the accumulation of oxalate oxidase (left) and TaPERO (right) mRNA in the leaf epidermis of transgenic plants, which carry the pPS24 or the pPS41 construct, by means of specific probes. W=RNA from whole leaf. E=RNA from leaf epidermis. EtBr=gel stained with ethidium bromide as loading control; 26S RNA=subsequent hybridization of the blot with a probe against the 26S ribosomal RNA as loading control.
  B) by means of real-time reverse PCR analysis
  The concentration of the TaPERO mRNA in whole leaf and epidermis of the transgenic line No. 2013 (transformed with the construct pPS41) was determined. The data were normalized by means of the constitutively expressed control genes UBC (ubiquitin-conjugating enzyme) and GAPDH (glyceraldehyde phosphate dehydrogenase). The expression remaining in the whole leaf comes from the non-removed upper leaf epidermis and from the phloem (side activity of the promoter).
  C) by means of real-time reverse PCR analysis
  Wild-type plants (Bobwhite) and the transgenic lines No. 2013 and No. 2151 (transformed with the pPS41 construct) were analyzed in the adult plant stage. The promoter is strongly expressed, in particular, in leaves and spikes. In stems and roots, the transgene is expressed not at all or only weakly.
13) Examination of mildew resistance of pPS41 transgenic plants
  The flag leaf of adult plants was cut away and inoculated with wheat mildew in a detached leaf assay together with Bobwhite wild-type plants. 7 days after inoculation, the mildew infection was evaluated. Mean values from 3 independent inoculation experiments with plants of the T2 and T3 generation are shown. Subline 2088/2 does not express any TAPERO and is not increased resistant. Mean value "non-silenced"=mean value of all lines except 2088/2 and all experiments.
14) Shoot growth of pPS41 transgenic plants
  Plants of the T2 generation were sown together with Bobwhite wild-type plants and photographed in the adult plant stage.
15) Examination of the mildew resistance of pWIR5-TaMlo-RNAi transgenic plants
  The flag leaf of adult plants of the T2 generation was cut away and inoculated with wheat mildew in a detached leaf assay together with Bobwhite wild-type plants. 7 days after inoculation, the mildew infection was evaluated. 2 sublines per line were tested in each case.

EXAMPLES

Figure 5B:
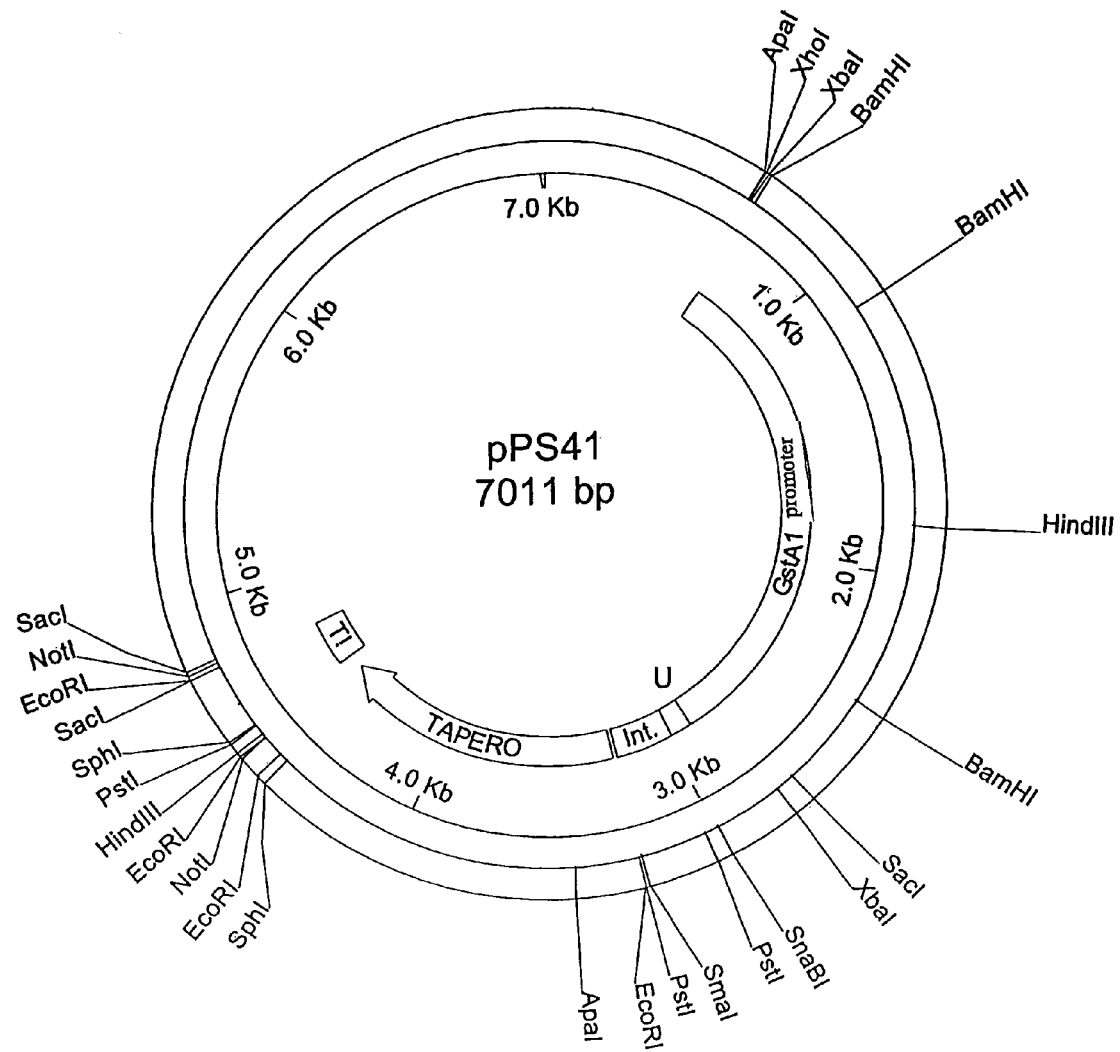
Figure 7B:
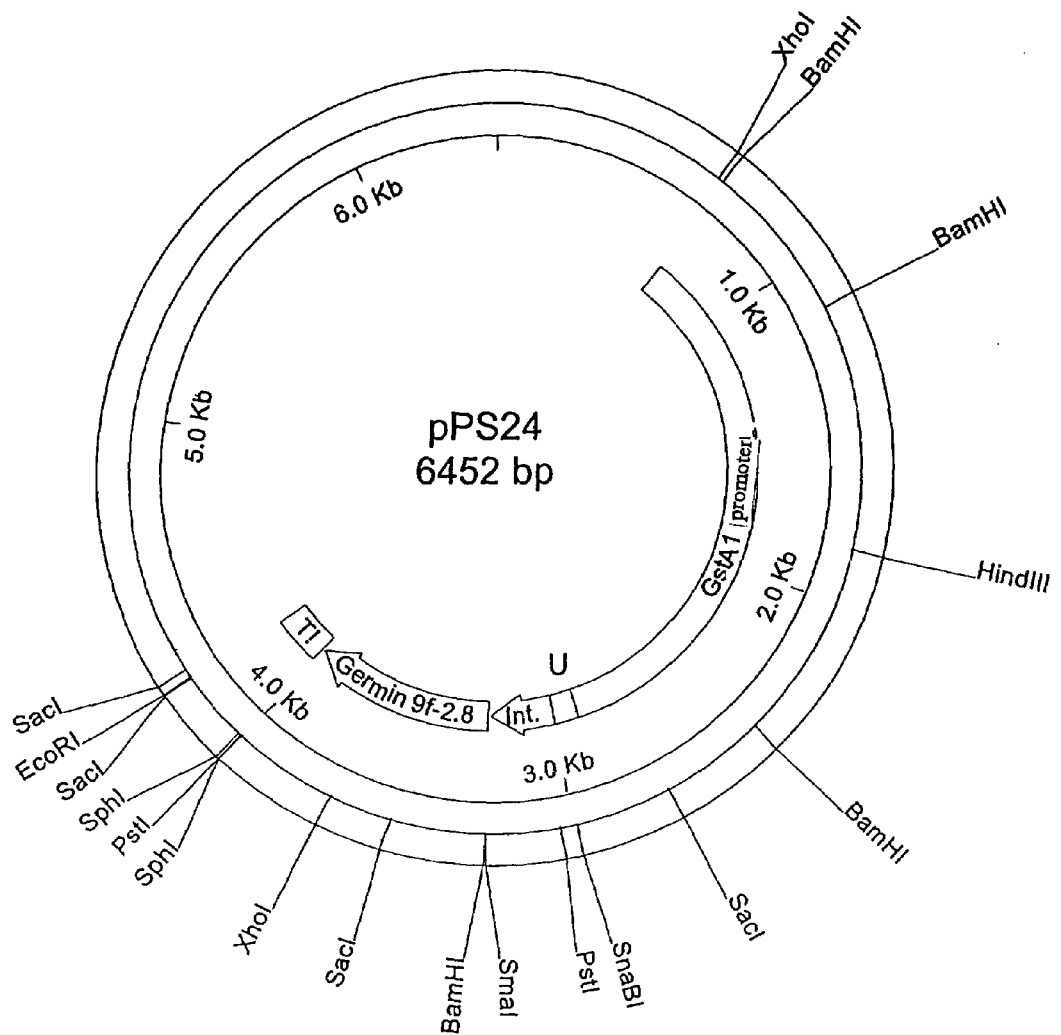
Figure 9B:
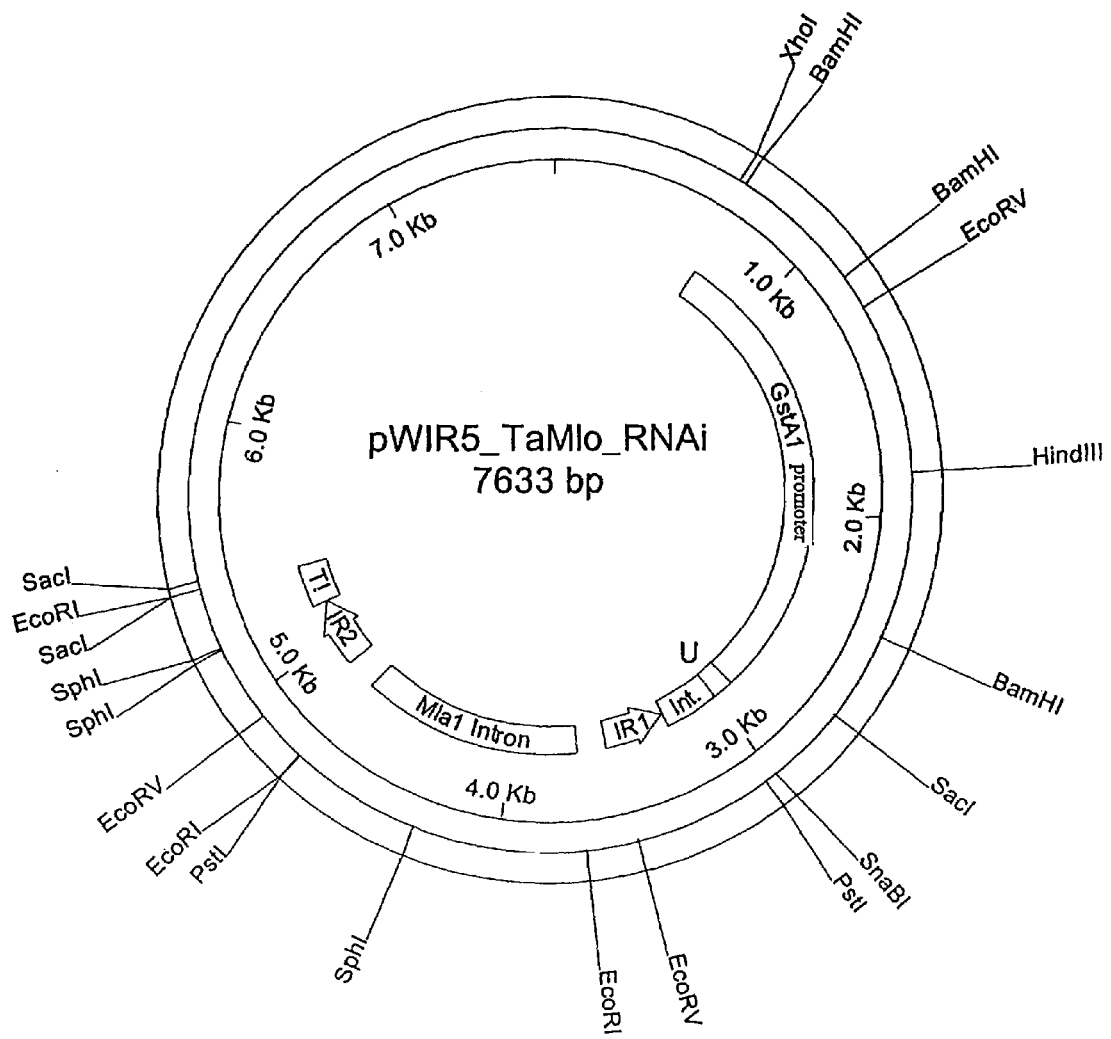
Figure 10:
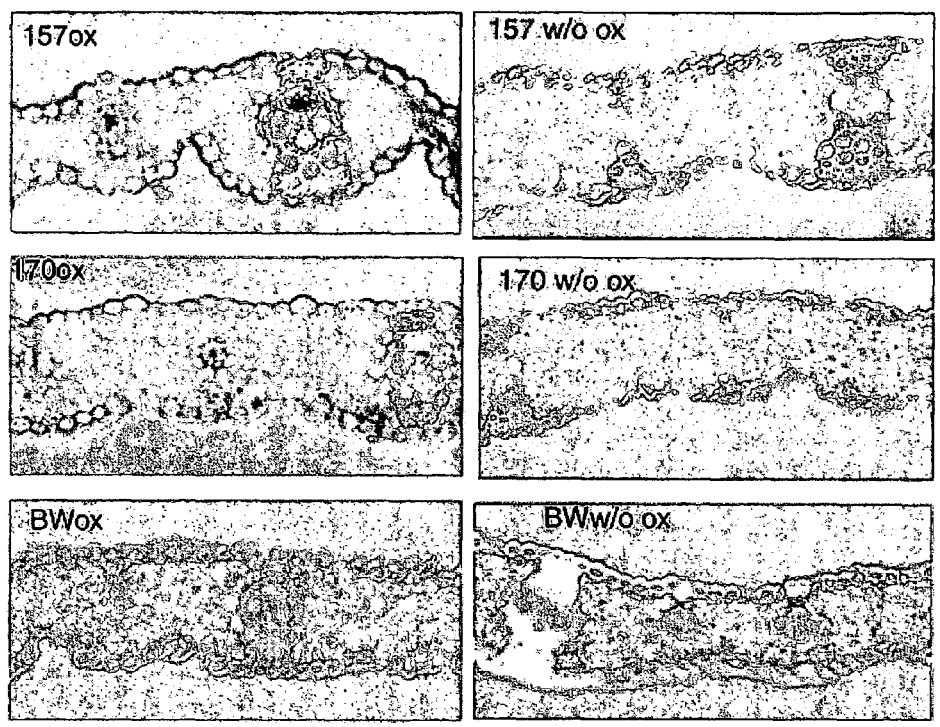
Figure 12:
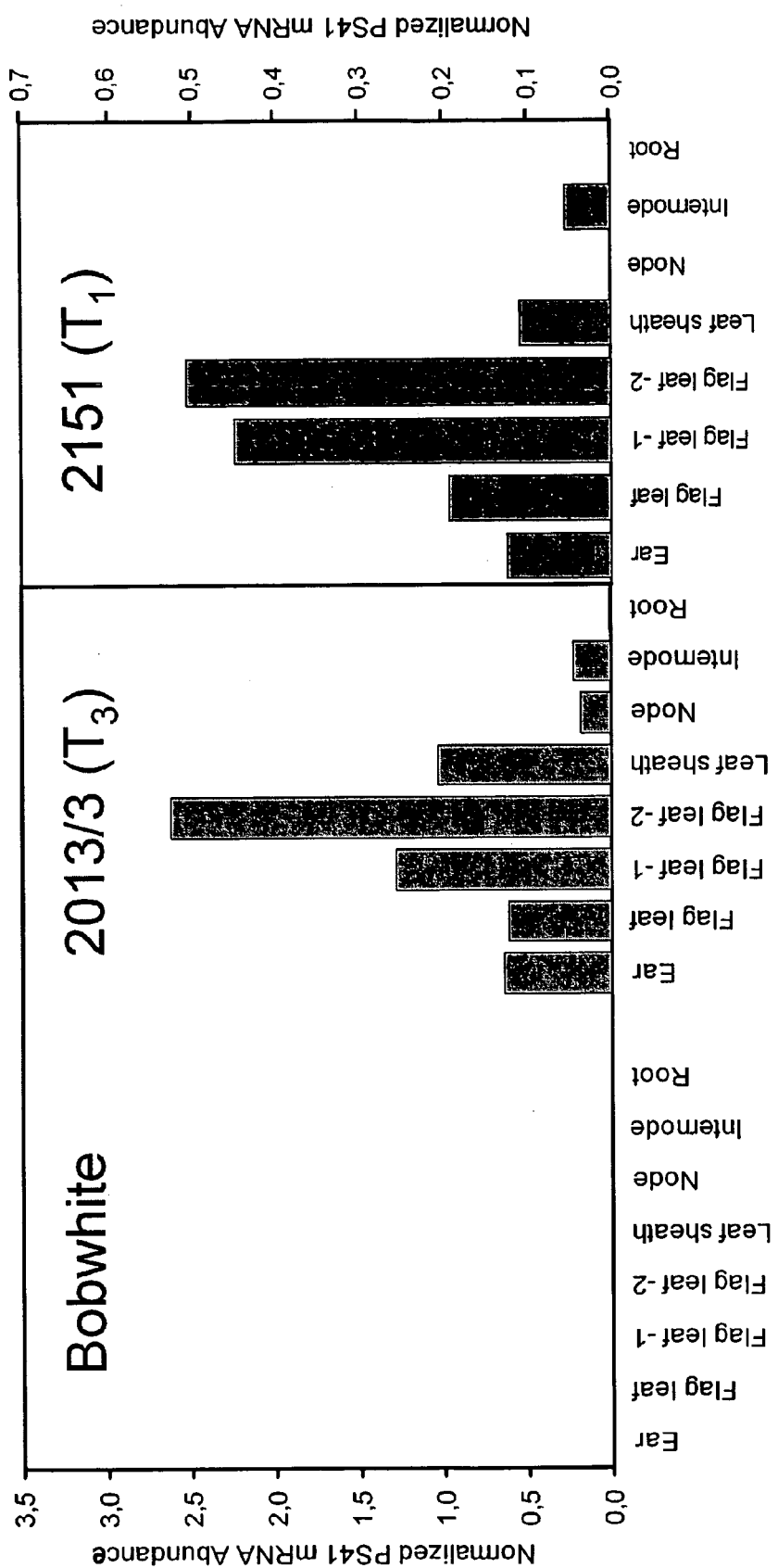
Figure 14:
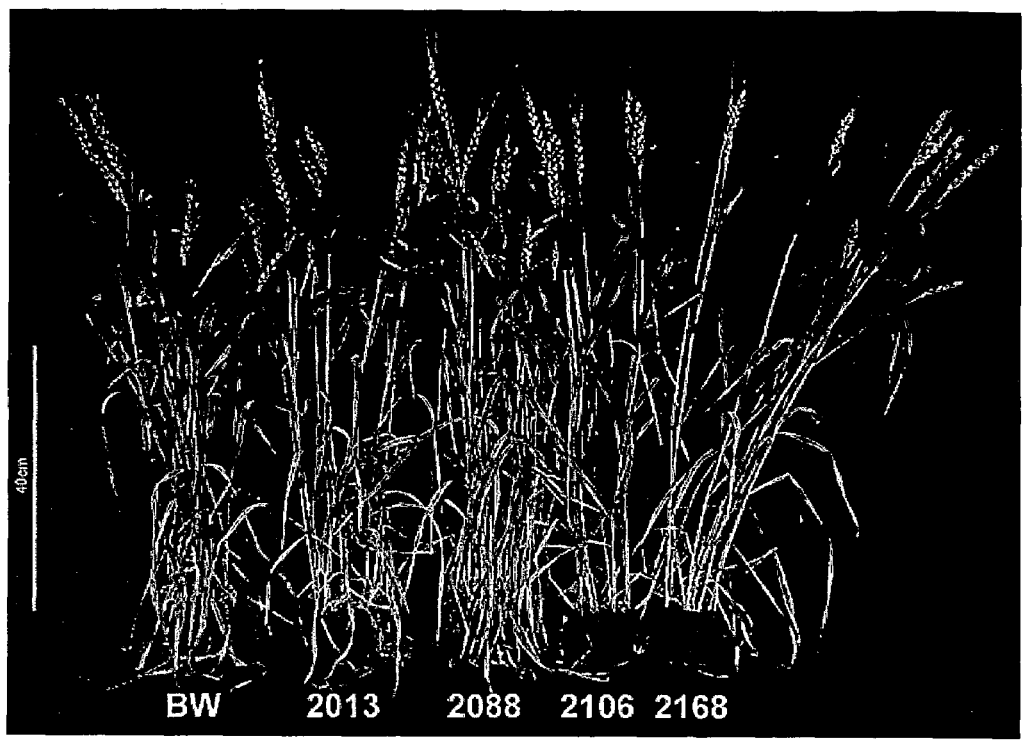
Figure 15:
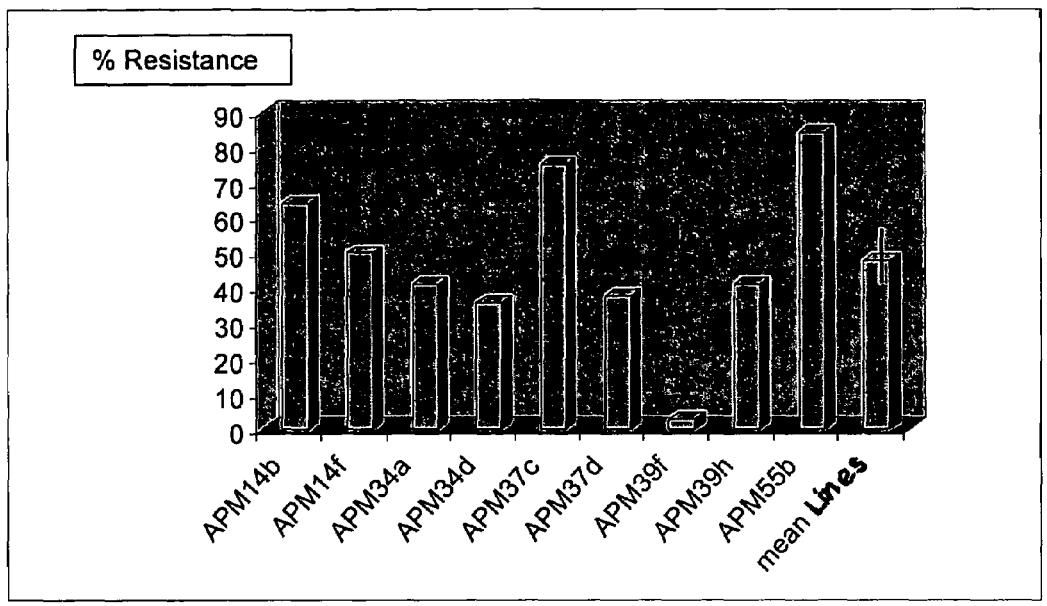

In the following examples, molecular biological standard methods like *E. coli* transformation, restriction digestion, ligation, DNA extraction, PCR, etc., as they are known in the art, were conducted according to Sambrook et al. (2001), vide supra. For all PCR reactions, proofreading Pwo polymerase (Roche) was used.

1) Generation of the Promoter Construct from GSTA1 Promoter and WIR1a Intron (pPS18)

Generation was conducted in several steps via the following precursor constructs: pPS1, pPS3, pPS15. All constructs contained the GUS reporter gene, so that they could be tested directly in a transient assay.

pPS1:

A 1.9 kb promoter fragment of the WIR1a gene was cut out of a recombinant pBluescript clone by means of PstI and cloned into the PstI restriction site of an expression cassette before the GUS gene. The expression cassette was based on pBluescript and contained the GUS gene followed by the transcription terminator of the wheat GSTA1 gene. As the GUS gene and the GSTA1 transcription terminator are no longer contained in the final constructs used (see Example 2), a detailed description of this expression cassette is omitted. The resulting construct contained a translational WIR1a:: GUS fusion.

pPS3:

With the adaptor primers 5' ATA TAT CTG CAG GGA GCC ACG GCC GTC CAC (SEQ ID No. 10) and 5' TAT CCC GGG CCC GTG CCT GGA CGG GAA (SEQ ID No. 11), a PCR fragment of about 240 bp was generated and its ends were cut with SmaI and PstI (via Adaptor). The genomic WIR1a clone served as PCR template. The PCR fragment contained the last 15 amino acids of the first exon of WIR1a and the intron including splice site acceptor, and was ligated in pPS1, cut with PstI (partially) and SmaI and purified by means of agarose gel electrophoresis. The resulting construct contained a translational WIR1a::GUS fusion with the WIR1 intron before the GUS gene. Furthermore, a deletion of amino acids Nos. 18-35 of the first exon of WIR1a was introduced in order to prevent the secretion of the WIR1a::GUS fusion protein (by means of removing the signal peptide).

pPS15:

The WIR1a promoter was replaced by a PCR fragment of the GSTA1 promoter. To this end, pPS3 was (partially) digested with XhoI and SnaBI and the vector band was purified by means of agarose gel electrophoresis. The GSTA1 promoter fragment of about 2.3 kb length was amplified by means of PCR with the adaptor primers 5' ATA TAT CTC GAG TCT AGA ACT AGT GGA TCC (SEQ ID No. 12) and 5' ATA TAT TAC GTA GTT TGT CCG TGA ACT TCA (SEQ ID No. 13) from the genomic GSTA1 clone and cut at the ends with XhoI und SnaBI. The PCR fragment was ligated with the gel-eluated pPS3 band, resulting in a translational fusion of the intron-containing WIR1a gene fragment with GUS under the control of the GSTA1 promoter.

pPS 18:

pPS15 was (partially) digested with PstI and SnaBI, the vector band was purified by means of agarose gel electrophoresis and ligated with a double-stranded oligonucleotide (5'GTA CAC AGG CAG CTA GCT CTC GAA ACC TCG CTC GAA ACG CA (SEQ ID No. 14) plus 5'CAT GTG TCC GTC GAT CGA GAG CTT TGG AGC GAG CTT TGC GT (SEQ ID No. 15)). This replaced the part of the WIR1a gene located around the translation start (46 bp upstream to 53 bp downstream of the translation start) with 42 bp of the 5'UTR of the WIR1a gene without the translation initiation codon ATG. The resulting construct contained a transcriptional fusion of the intron-containing WIR1a gene fragment with GUS under the control of the GSTA1 promoter.

2) Generation of the Constructs Used a) expression vector pPS24 (oxalate oxidase expression under the control of the promoter according to the present invention)

A HindIII/SphI fragment of 745-bp length of the wheat gf-2.8 gene (oxalate oxidase; Acc. No. M63223) containing the entire open reading frame (ORF) was subcloned into the plant expression cassette pGY1, which resulted in the construct pGermin (described in Schweizer et al., 1999). For this cloning, the oxalate oxidase fragment was ligated into an intermediate vector in order to be able to ligate the fragment by means of the restriction sites BamHI and PstI in pGY1.

From pGermin, a SmaI/EcoRI fragment of about 1 kb length, which contained the oxalate oxidase gene and the CamV 35S terminator, was ligated into the vector pPS18, which was SmaI/EcoRI-cut and purified by means of agarose gel electrophoresis. The resulting construct contained a transcriptional fusion of the intron-containing WIR1a gene fragment with the oxalate oxidase gene under the control of the GSTA1 promoter. Compared to pPS18, the construct did no longer contain the GSTA1 transcription terminator, but the transcription terminator of the CamV 35S gene.

b) expression vector pPS41 (TAPERO expression under the control of the promoter according to the present invention)

From pWIR3 (containing a transcriptional fusion of the CamV 35S promoter and TAPERO; Schweizer et al., 1999), a TAPERO fragment of about 1.2 kb length was isolated using SmaI and PstI by means of restriction digestion. The TAPERO fragment was ligated in vector pPS24, which was (partially) digested with SmaI and PstI and was purified by means of agarose gel electrophoresis. This resulted in a transcriptional fusion of the intron-containing WIR1a gene fragment with the TAPERO gene (Acc. No. X56011) under the control of the GstA1 promoter, in which the oxalate oxidase gene was substituted by the TAPERO gene. Like pPS24, pPS41 contains the transcription terminator of the CamV 35S gene.

c) expression vector pWIR5-TaMlo-RNAi (expression of the Mlo-RNAi construct under the control of the promoter according to the present invention)

First, the third intron of the Mla1 resistance gene from barley (about 1.1 kb), which was subcloned in the vector pGEM Teasy, was isolated by means of EcoRI and PstI and was ligated into the vector pBSw41 (pBluescript derivative with partial TaMlo1 cDNA, cloned by Candace Elliott within the scope of her dissertation; GenBank accession No. AF361933), which was also EcoRI- and PstI-cut.

From this construct, the Mla1 intron together with a part of the coding sequence of the TaMlo1 gene was isolated as an about 1.55 kb PstI/MscI fragment (=fragment 1). Parallel to this, a fragment of about 450 bp was amplified by means of PCR from the plasmid pBSw41 with the oligonucleotides T3 (standard sequencing primer for pBluescript) and TaMlo1-1 (5' GTC GCATGC CTG TCC ACA CGA AAT GTG C 3' (SEQ ID No. 16), SphI, restriction site underlined). Subsequently, the PCR fragment was digested by means of the restriction enzymes PstI and SphI (=fragment 2). The vector pPS24 (promoter +oxalate oxidase, see above) was opened by means of restriction digestion with SmaI and SphI and the oxalate oxidase gene fragment, which was cut out, was discarded. Thereupon, the above-described fragments 1 and 2 were ligated into the SmaI/SphI-cut vector pPS24 in a three-component ligation. In this ligation, the ends of the MscI and SmaI-cut components are compatible, as both are so-called blunt ends. The resulting construct (pTaMlo1RNAi) contains about 300 bp of the TaMlo1 gene as well as about 150 bp polylinker/adaptor sequence as "inverted repeats", separated by the Mla1 intron. The control of this transcription unit is subject to the GSTA1 promoter.

Annotation: The gene herein referred to as TaMlo1 for historical reasons was later named TaMloA1 (Elliott et al., 2002). Mol. Plant Microbe Interact. 15: 1069-1077 (2002).

3) Transformation of the Wheat Plants

Wheat plants (cv. Bobwhite) were raised in phytochambers for 40 days at 15° C. during daytime and 12° C. during nighttime under short day conditions (10 h/d, about 600 HE) and subsequently in a greenhouse at 18/16° C. and a photoperiod of at least 16 h. The spikes were either used immediately or stored for up to 5 days at 4° C. The caryopses taken from the spike were surface-sterilized for 2 minutes with 70% ethanol and then for 15 to 20 minutes in 5% sodium hypochlorite solution/0.1%-Tween 20 and finally washed four times with sterile aqua bidest.

Unripe embryos having a size of 0.5 to 1.5 mm were prepared out of the caryopses under sterile conditions and were laid out on callus-inducing medium in petri dishes with their scutellum facing upward (basic medium according to Murashige Skoog (1962) with 2 mg/l 2,4-D, 40 g maltose monohydrate, 500 mg/l L-glutamine, 100 mg/l casein hydrolysate, 5 µM $CuSO_4$ and 0.25% phytagel). The cultures were incubated in the dark at 25° C.

The biolistic transformation was conducted five to seven days after isolating the embryos. Four to six hours prior to particle bombardment, the already proliferating embryos were transferred to a new medium having reduced water potential (as above, supplemented with 0.3 M mannitol) and incubated in the dark at 25° C.

The plasmid pAHC20 (Christensen and Quail 1996), which contains the bar-gene encoding phosphinothricin acetyltransferase, was mixed in a molar ratio of 1:1 with a vector to be co-transformed. Altogether, 10 µl plasmid DNA solution were then precipitated onto the particles of 25 µl of a 60 mg/l gold suspension. For one bombardment, 30 jig particles in 5 µl ethanol were applied onto a micro carrier. Bombardment was conducted according to the specifications of the manufacturer of the DuPont PDS-1000/He.

Twelve to 16 hours after particle bombardment, the explants were transferred to new callus-inducing medium (as for the pre-culture of the embryos) and incubated for 10 days in the dark at 25° C.

The calli were then transferred to differentiation medium (basic medium according to Murashige and Skoog (1962) with 20 g/l sucrose, 5 µM $CuSO_4$, 0.25% phytagel and 3 mg/l bialaphos) and were incubated with a photoperiod of 16 h at 200 µE and 25° C.

After 2 weeks, the transfer of the non-browned calli to regeneration medium (basic medium according to Murashige and Skoog (1962) with 20 g/l sucrose, 0.25% phytagel and 4 mg/l bialaphos) and a further incubation with a photoperiod of 16 h at 200 µE and 25° C. was conducted.

After another 2 weeks, the grown shoots were thinned out, transferred to culture tubes containing regeneration medium and further cultivated with a photoperiod of 16 h at 200 µE and 25° C.

Identification of transgenic regenerates was conducted by means of the PAT activity test of leaf extracts according to Spencer et al. (1990) or by means of amplifying transgene-specific sequences from genomic DNA of the candidate plants and/or Southern blot with the use of a corresponding probe.

Depending on the quality of the basic material, the transformation efficiency of the method amounted to 0.5 to 3 transgenic plants per 100 embryos cultivated.

4) In Situ Oxalate Oxidase Activity in Plants having the pPS24 Construct

Leaf segments of Bobwhite wild-type plants or of pPS24 transgenic wheat plants of the T3 generation were infiltrated in vacuum with oxalate oxidase detection solution (2.5 mM oxalic acid, 3.5 mM free EDTA, 0.6 mg/ml 4-chloro-1-naphthol, 50 µg/ml peroxidase from horseradish, 20% v/v ethanol, adjusted to pH 4.0 by means of Tris base) and incubated overnight at +37° C. After removal of the detection solution, the leaves were incubated for another 24 h at +4° C. in $H_2O$. Subsequently, the leaves were manually crosscut into thin segments and microscopized. Phase contrast light microscopy was conducted in a Zeiss Axiophot at 100-fold magnification. Cells with oxalate oxidase expression have cell walls stained violet.

5) Detection of the TAPERO Transgene in pPS41 Transgenic Plants by Means of Northern Blot Analysis Leaves of Bobwhite plants and of pPS41 transgenic plants of the T2 generation (about 1 g fresh weight in each case, FW), both in the flag leaf stage, were homogenized in liquid nitrogen until a fine powder formed. The powder was added to 3 ml RNA extraction buffer (0.5 M Tris Cl pH 8.0; 0.25 M Na-EDTA; 5% (w/v) SDS) and 1.5 ml buffer-saturated phenol (15 ml plastic tubes) and well shaken. The extracts were centrifuged for 30 min at 4000 rpm-5000 rpm, 20° C. (swing out, Heraeus Varifuge). 1.5 ml chloroform were added (without draining the supernatant) and the tube was inverted several times. The extracts were re-centrifuged for 30 min at 4000 rpm-5000 rpm, 20° C., and the supernatant was carefully poured into a new tube (15 ml plastic tube). The RNA was precipitated by means of adding 3 ml 6 M LiCl (overnight, 4° C.). The precipitated RNA was centrifuged for 30 min at 12,500 rpm, 4° C. (fixed rotor, Hermle Z360K), the RNA pellets were taken up in 500-1000 µl 70% ethanol (RNA does not dissolve) and transferred to Eppendorf tubes. The samples were centrifuged for 10 min at 14,000 rpm, 4° C. (fixed rotor, Eppendorf Centrifuge 5417R), and the supernatant was lifted off. The RNA pellets were dried for 5 min at 37° C., taken up in 100 µl to 200 µl TE, and dissolved for 5 to 10 min at −75° C. The denaturing agarose gel electrophoresis of the RNA in formaldehyde-containing gels and the transfer to nylon membranes (Hybond N, Amersham) was conducted according to standard protocols (Sambrook et al., vide supra). 10 µg RNA were applied per sample. Radioactive probe labeling with $\alpha$ $^{32}$P-dCTP was conducted according to the random prime labeling method using a kit (Roche). Hybridization was conducted overnight at 65° C. in CHURCH buffer (0.5 M Na phosphate pH 7.2; 1% (w/v) BSA; 7% (w/v) SDS; 1 mM $Na_2ETDA$). The blots were washed twice for 15 min in washing solution (0.1×SSC; 0.1 5 w/v) SDS) at 65° C. and subsequently exposed for 16 to 48 h against phosphorimager screens. The exposed screens were scanned by means of a phosphorimager device (FujiFilm FLA 3000) and exported as image files in TIFF format.

6) Detection of the TAPERO Transgene in pPS41 Transgenic Plants by Means of Western Blot Analysis Leaf tips of Bobwhite plants and of pPS41 transgenic plants of the T2 generation, both in the flag leaf stage, were homogenized in IWF buffer (32 mM Na-phosphate; 84 mM citrate; pH 2.8; spatula tip polyvinylpolypyrrolidone). The homogenates were centrifuged for 15 min at 13,000 rpm and 4° C. The supernatants were mixed with 0.5 g/ml ammonium acetate and acid-soluble proteins were precipitated overnight at 4° C.

The proteins were centrifuged for 30 min at 13,000 rpm and 4° C. The protein pellets were taken up in 50 µl/g FG re-suspension buffer (50 mM Tris-Cl pH 7.5; 20% (v/v) glycerol). 5 µl 4-fold concentrated SDS sample buffer were added to 20 µl sample and the samples were mixed with (1-5 µl) saturated Tris solution until the color of bromphenol blue changed to blue. For each lane, 12.5 µl boiled sample were separated in denaturing SDS polyacrylamide gel electrophoresis (15% separating gel) according to a standard method using mini-gel equipment by Bio-Rad.

Subsequent to electrophoresis, the gels were either Coomassie-stained (as loading control) or transferred according to a standard method to a nitrocellulose membrane (blotted). According to a standard method, the membranes were incubated with a first polyclonal antibody (dilution 1:2000), which was directed against the Prx8 protein from barley (a protein homologous to TAPERO), followed by the second antibody (dilution 1:2000), which was directed against rabbit antibodies and to which alkaline phosphatase was coupled. The TAPERO protein bands were detected by means of localized alkaline phosphaltase activity (BCIP/NBT staining solutions; prefabricated tablets (Roche)).

7) Detection of the Epidermis-specific Transgenic Expression by Means of Northern Blot Analysis and Real-time PCR Analysis RNA extraction and Northern blot analysis were conducted as described in Example 5. Real-time PCR analysis was conducted by means of a LightCycler® device (Roche, Mannheim, Germany) according to the manufacturer's specifications.

8) Mildew Resistance in pPS41 or pWIR5-TaMlo-RNAi Transgenic Plants

For the resistance test, adult pPS41 or pWIR5-TaMlo-RNAi transgenic wheat plants were used, which had been grown in the greenhouse and had a fully developed freshly grown flag leaf. Simultaneously grown wild-type plants cv. Bobwhite served as controls. The apical half of the flag leaf was cut off and spread on 0.5% (w/v) phytoagar, which was mixed with 20 ppm benzimidazole, in 20×20 cm large polycarbonate dishes. One transgenic subline (20 leaves each) plus Bobwhite wild-type (6 leaves each) was spread per dish. The leaf segments were inoculated with mildew spores in an inoculation medium by means of blowing spores of 4 strongly inoculated wheat leaves into the tower. After 5 min, the dishes were removed, sealed, and incubated at 20° C. in indirect daylight. Seven days after inoculation, the mildew infection was evaluated using a class evaluation system (Schweizer et al., 1995). Resistance was calculated with reference to the control leaves located on each respective phytoagar plate.

LITERATURE

Christensen and Quail (1996) Transgenic Res. 5: 213-218.

Elliott et al., (2002). Molecular Plant Microbe Interactions 15: 1069-1077.

Murashige and Skoog (1962) Physiologia Plantarum 15: 473-497.

Schweizer, P., Vallélian-Bindschedler, L., and Mösinger, E. (1995). Heat-induced resistance in barley to the powdery mildew fungus *Erysiphe graminis* f.sp. *hordei*, Physiological and Molecular Plant Pathology 47, 51-66.

Schweizer, P., Pokorny, J., Abderhalden, O., and Dudler, R. (1999). A transient assay system for the functional assessment of defense-related genes in wheat, Mol Plant-Microbe Interact 12, 647-654.

Spencer et al. (1990) TAG 79: 625-631.

The invention claimed is:

1. A method of causing epidermis specific expression of a desired coding sequence in a transgenic plant, the method comprising introducing into a plant cell a chimeric gene comprising an isolated promoter region that controls epidermis-specific expression operably linked to the desired coding sequence, said promoter region comprising a first sequence originating from the promoter of a GSTA1 gene and a second sequence originating from the intron of a WIR1a gene, wherein the first sequence is SEQ ID No. 1 and the second sequence is SEQ ID No. 2 or wherein the first sequence has at least 95% sequence identity to SEQ ID No. 1 and the second sequence has at least 95% sequence identity to SEQ ID No. 2.

2. A method for increasing pathogen resistance in a plant, the method comprising transforming a plant cell with a chimeric gene comprising an isolated promoter region that controls epidermis-specific expression operably linked to a DNA encoding a protein that confers pathogen resistance, said promoter region comprising a first sequence originating from the promoter of a GSTA1 gene and a second sequence originating from the intron of a WIR1a gene, wherein the first sequence is SEQ ID No. 1 and the second sequence is SEQ ID No. 2 or wherein the first sequence has at least 95% sequence identity to SEQ ID No. 1 and the second sequence has at least 95% sequence identity to SEQ ID No. 2; and regenerating a transformed plant from the transformed plant cell; said transformed plant exhibits increased resistance to a pathogen.

3. The method according to claim 1, wherein the first sequence is SEQ ID No. 1 and the second sequence is SEQ ID No. 2.

4. The method according to claim 2, wherein the first sequence is SEQ ID No. 1 and the second sequence is SEQ ID No. 2.

5. The method according to claim 1, wherein said isolated promoter region comprises the nucleic acid sequence of SEQ ID NO. 3, or has at least 95% sequence identity to the nucleic acid sequence of SEQ ID No. 3.

6. The method according to claim 2, wherein said isolated promoter region comprises the nucleic acid sequence of SEQ ID NO. 3, or has at least 95% sequence identity to the nucleic acid sequence of SEQ ID No. 3.

7. The method according to claim 1, wherein the desired coding sequence originates from a resistance gene.

8. The method according to claim 7, wherein the coding sequence encodes a peroxidase or an oxalate oxidase.

9. The method of claim 1, wherein the coding sequence is in antisense orientation.

10. A transgenic plant produced by the method of claim 1.

11. A transgenic plant produced by the method of claim 2.

12. The transgenic plant of claim 10, wherein said plant is a monocot or dicot plant.

13. The transgenic plant of claim 11, wherein said plant is a monocot or dicot plant.

14. The transgenic plant according to claim 12, wherein said plant is poaceae.

15. The transgenic plant according to claim 13, wherein said plant is poaceae.

16. The transgenic plant according to claim 14, wherein said plant is wheat or barley.

17. The transgenic plant according to claim 15, wherein said plant is wheat or barley.

* * * * *

UNITED STATES PATENT AND TRADEMARK OFFICE
CERTIFICATE OF CORRECTION

PATENT NO. : 7,608,756 B2 Page 1 of 1
APPLICATION NO. : 10/574740
DATED : October 27, 2009
INVENTOR(S) : Schweizer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1 days.

Signed and Sealed this

Twelfth Day of October, 2010

David J. Kappos
*Director of the United States Patent and Trademark Office*

```
                        SEQUENCE LISTING

<160> NUMBER OF SEQ ID NOS: 15

<210> SEQ ID NO 1
<211> LENGTH: 2198
<212> TYPE: DNA
<213> ORGANISM: Triticum sp.

<400> SEQUENCE: 1
gacgccgaag tggagccgac agcccccagg tcccaagccc tcggcagact agatcactag      60
ccctggatcg gcgaggtgac tggatgacga gcagcacctg gtctggcggg tgttgggcga     120
gtagaaccag gggcgatggc gacgcgctga ccttctcccc tcaccggcga tctgctcctt     180
ctgggtgggg gtcgccggct gacgttctgt tgcggggtgg gggtcgccgg ctggcgttct     240 gctgcgggt  gggagtcgcc gaccggcgtg ctgctgctag gacaatcggt gaggccagtt     300
aggtgctagc cgatcgattg gcgaagagat ccgagtcctg gggagatcag tgaggccagg     360
tgctatttgg cctatcaatt ggccaggttc tgggaacggg gcgtggcgtg atcaacgagg     420
tgctaggctg ctagctaggg aactggatcc tggaacgtgg aggaggcaag tccggtatgc     480
taagtacttt aactttcctt cttcacatcc acctgattca gattattttg atctaaatta     540
acttgcaaaa aatatatgtg tgatatccat ctactataat tgcttacaat caaaattata     600
tgtgattttt tttagtttag aagatttata tgcacagtaa atctgaatgt tcttcacatg     660
catgatttag tttaacttta aagagttata ctaactagtc ttgataaaga gatcttttgg     720
agcaacacca aacctcgtga ggtgttttgc ctacggaaag gttgtgctat gtaatgatta     780
ttattaggat caaagttgta ggataaacgt aaaaccttct cgatgtatct tttatacaac     840
attgtagttt agttatatat ggagagagtg atttaacact ttgtgtttaa gagtagaata     900
```

```
agttattcca cactctagcc aaacgaacta tttggcaaat atctcgctag ctggtgagag    960
ccagagccgt ggaaagtctg tcttgctatt aaggcacaag catcaaacag gaacatttag   1020
agccatggaa aagtgatgtg tcgcctacca atgggccaac tgctagcgat gtaataatag   1080
catccaagtt gattttttat agaacatgca aggcgttggc aagtgggaaa atgattgatc   1140
gctggcaagc ttaactctcg gaacttatag cattcaactg aatcagaaca agattaaaa    1200 aaaaatacat ttccatcgat agtgaaaaat tattcaattg agtgacaacg aaaatcatat   1260
tggaatgtac atttacttgt tgatttaaa ttagaggcat ttttctacct tttttagtta    1320
ataagatatg catataccca cccttagtgt tttcgagaca acgagagggc acattgcttt   1380
tggtgctacc atctctctca agcctcaaat aagttgtgcg acacgatta tcttcccgcg    1440 ttggaatatc gtggcctggt agagctagcg aaaaatcttc catgttggaa tatgtcggca   1500
gccggatagc cgccatgcat gtaaagtctc ttttacctt acacttgctc aagtgacact    1560
gtatgtcgcc taccacttgc taaatcaatg ggccaactgc tagcgacgta atagtagcaa   1620
gttgatttac agtgttttgc tacagttctc tgactttgtt tcttcatttt agactagctg   1680
actactgtcg cttacctgcc ttcccttctc cacgttagag gatccagttc tgatattgag   1740
acctcgacga tgggaggaag ggcgcgatcg atgtggagta atttgaattt caaatctatc   1800
tatctggggt atattggtcc ttcaccgatg tttgggggc tgtcggaaat tggttccgcg    1860
atctacaaaa gtgaatggag ggagtagttg tttctccaat ccgtaccaac gcacgtgttt   1920
ctaactagta cttacttcct tcgcaccaca atatggaata gagggagtat cgataaacta   1980
acaaagatga ttacttaccc ggtttaaatg attcaagagc tcatttaatt tggcactcat   2040
catttcatat atctttttg gtagaaatga aataaagcag atctagacac tagctaaaaa    2100
gtcgatgtag ccttgttatt ccttgggcc acgcgggccg ggtgtggtgc tccctgctct    2160
gtgtataaat ggagatcaac atccaaggcc tcctccca                            2198

<210> SEQ ID NO 2
<211> LENGTH: 114
<212> TYPE: DNA
<213> ORGANISM: Triticum sp.

<400> SEQUENCE: 2
gtcagtcgtc ggacggtgtc cgttcatttc ctccccattt ttgtaattga ttaacttgtt     60
atacatgctg acctcgacct gctgaataac gtccgtccat ggtttcccgt ccag           114

<210> SEQ ID NO 3
<211> LENGTH: 2553
<212> TYPE: DNA
<213> ORGANISM: Triticum sp.

<400> SEQUENCE: 3
gacgccgaag tggagccgac agccccagg tcccaagccc tcggcagact agatcactag      60
ccctggatcg gcgaggtgac tggatgacga gcagcacctg gtctggcggg tgttgggcga    120
gtagaaccag gggcgatggc gacgcgctga ccttctcccc tcaccggcga tctgctcctt    180
ctgggtgggg gtcgccggct gacgttctgt tgcggggtgg gggtcgccgg ctggcgttct    240
gctgcggggt gggagtcgcc gaccggcgtg ctgctgctag gacaatcggt gaggccagtt    300
aggtgctagc cgatcgattg gcgaagagat ccgagtcctg gggagatcag tgaggccagg    360
tgctatttgg cctatcaatt ggccaggttc tgggaacggg gcgtggcgtg atcaacgagg    420
tgctaggctg ctagctaggg aactggatcc tggaacgtgg aggaggcaag tccggtatgc    480
```

-continued

```
taagtacttt aactttcctt cttcacatcc acctgattca gattattttg atctaaatta      540
acttgcaaaa aatatatgtg tgatatccat ctactataat tgcttacaat caaaattata      600
tgtgattttt tttagtttag aagatttata tgcacagtaa atctgaatgt tcttcacatg      660
catgatttag tttaacttta aagagttata ctaactagtc ttgataaaga gatcttttgg      720
agcaacacca aacctcgtga ggtgttttgc ctacggaaag gttgtgctat gtaatgatta      780
ttattaggat caaagttgta ggataaacgt aaaaccttct cgatgtatct tttatacaac      840
attgtagttt agttatatat ggagagagtg atttaacact ttgtgtttaa gagtagaata      900
agttattcca cactctagcc aaacgaacta tttggcaaat atctcgctag ctggtgagag      960
ccagagccgt ggaaagtctg tcttgctatt aaggcacaag catcaaacag gaacatttag     1020
agccatggaa aagtgatgtg tcgcctacca atgggccaac tgctagcgat gtaataatag     1080
catccaagtt gatttttat agaacatgca aggcgttggc aagtgggaaa atgattgatc      1140
gctggcaagc ttaactctcg gaacttatag cattcaactg aatcagaaca agattaaaa      1200 aaaaatacat ttccatcgat agtgaaaaat tattcaattg agtgacaacg aaaatcatat     1260
tggaatgtac atttacttgt tgattttaaa ttagaggcat ttttctacct tttttagtta     1320
ataagatatg catataccca cccttagtgt tttcgagaca acgagagggc acattgcttt     1380
tggtgctacc atctctctca agcctcaaat aagttgtgcg gacacgatta tcttcccgcg     1440
ttggaatatc gtggcctggt agagctagcg aaaaatcttc catgttggaa tatgtcggca     1500
gccggatagc cgccatgcat gtaaagtctc ttttacctt acacttgctc aagtgacact      1560
gtatgtcgcc taccttgc taaatcaatg ggccaactgc tagcgacgta atagtagcaa       1620
gttgatttac agtgttttgc tacagttctc tgactttgtt tcttcatttt agactagctg     1680
actactgtcg cttacctgcc ttcccttctc cacgttagag gatccagttc tgatattgag     1740
acctcgacga tgggaggaag ggcgcgatcg atgtggagta atttgaattt caaatctatc     1800
tatctggggt atattggtcc ttcaccgatg tttgggggc tgtcggaaat tggttccgcg      1860
atctacaaaa gtgaatggag ggagtagttg tttctccaat ccgtaccaac gcacgtgttt     1920
ctaactagta cttacttcct tcgcaccaca atatggaata gagggagtat cgataaacta     1980
acaaagatga ttacttaccc ggtttaaatg attcaagagc tcatttaatt tggcactcat     2040
catttcatat atcttttttg gtagaaatga aataaagcag atctagacac tagctaaaaa     2100
gtcgatgtag ccttgttatt tccttgggcc acgcgggccg ggtgtggtgc tcccgctct      2160 gtgtataaat ggagatcaac atccaaggcc tcctcccaca cacacgct acagagcaga       2220 gcagagtctt gctccagtat ctgccctctc ctgcctgcct gtagagcatc catcacgtga     2280
agttcacgga caaactacgt acacaggcag ctagctctcg aaacctcgct cgaaacgcac     2340
ctgcagatcg ctctcttcgt cgtcgtcgcc gcgatcatca tcaacagctc cgtctgcctt     2400
ggagccacgg ccgtccacga cgccgccgcc tcaggtcagt cgtcggacgg tgtccgttca     2460
tttcctcccc attttgtaa ttgattaact tgttatacat gctgacctcg acctgctgaa      2520
taacgtccgt ccatggtttc ccgtccaggc acc                                  2553
```

<210> SEQ ID NO 4
<211> LENGTH: 1246
<212> TYPE: DNA
<213> ORGANISM: Triticum sp.

<400> SEQUENCE: 4

| | |
|---|---|
| accaccacac cactccacca gtaagaagtg cagcaggtag ctagtaagcc ggcgtagctt | 60 |
| tgctcttgca gctagctagc taaccatggc cgcctctgcc tcttgccttt ctcttgtggt | 120 |
| gctcgtggct ctggccacgg cggcgtcggc gcagctgtca ccgaccttct acgacacgtc | 180 |
| ctgccccagg gccctggcca tcatcaagag tggcgtcatg gccgccgtga gcagcgaccc | 240 |
| tcggatgggc gcgtcgctgc tccggctgca cttccacgac tgcttcgtcc aaggctgcga | 300 |
| cgcgtctgtt ttgctgtctg gcatggaaca aaatgctatc ccgaacgcgg ggtcgctgag | 360 |
| gggcttcggc gtcatcgaca gcatcaagac gcagatcgag gccatctgca atcagaccgt | 420 |
| ctcctgcgcc gacatcctca ccgtcgccgc ccgtgactcc gttgtagccc tcggagggcc | 480 |
| gtcatggaca gtccctctgg ggagaagaga ttccacagat gcaaacgagg cggcggcaaa | 540 |
| cagcgacctg ccaggcttta catctagccg gtcagatctt gagctggcat tcagaaacaa | 600 |
| gggcctcctt acgatcgaca tggtggccct ctcgggcgcg cacaccatcg gccaggcgca | 660 |
| gtgtgggacc tttaaggaca ggatctacaa tgagactaac atcgcacgg ccttcgccac | 720 |
| atctctccgg gccaactgcc ccaggtcaaa cggcgacggg agcctggcga acctggacac | 780 |
| gacgacggcc aacacgttcg ataacgccta ctacaccaac ctcatgtcac agaagggct | 840 |
| cctgcactcg gaccaggtgc tgttcaacaa cgacaccacc gacaacactg tccggaactt | 900 |
| tgcgtcgaac ccagcggcgt tcagcagcgc cttcacgacc gccatgatca agatgggcaa | 960 |
| catcgcgccg aagacaggca cgcaggggca gatcaggctc agctgctcca gggtgaactc | 1020 |
| gtgattgata gacgagttac tgcatactag ccagcacgac acgtacgtga atgaataagg | 1080 |
| ccacagaacc agtggccaat ataaatacca gctcttgaaa ccgtgtattt tatgtacgag | 1140 |
| tagcagcaaa tcatgcatgc atctacacat atatatgtaa cgatcgaatt cccactttct | 1200 |
| catgcaaagg catggagaat tactatcaat cttagttata cgtgta | 1246 |

<210> SEQ ID NO 5
<211> LENGTH: 7011
<212> TYPE: DNA
<213> ORGANISM: Triticum sp.

<400> SEQUENCE: 5

| | |
|---|---|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gataggggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta atcggaaccc ctaaagggag | 300 |
| ccccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg tttcccagt cacgacgttg | 600 |
| taaaacgacg gccagtgagc gcgcgtaata cgactcacta tagggcgaat tgggtaccgg | 660 |
| gccccccctc gagtctagaa ctagtggatc cccgacgccg aagtggagcc gacagccccc | 720 |
| aggtcccaag ccctcggcag actagatcac tagccctgga tcggcgaggt gactggatga | 780 |
| cgagcagcac ctggtctggc gggtgttggg cgagtagaac caggggcgat ggcgacgcgc | 840 |
| tgaccttctc ccctcaccgg cgatctgctc cttctgggtg ggggtcgccg gctgacgttc | 900 |

-continued

```
tgttgcgggg tggggtcgc cggctggcgt tctgctgcgg ggtgggagtc gccgaccggc      960
gtgctgctgc taggacaatc ggtgaggcca gttaggtgct agccgatcga ttggcgaaga     1020
gatccgagtc ctggggagat cagtgaggcc aggtgctatt tggcctatca attggccagg     1080
ttctgggaac ggggcgtggc gtgatcaacg aggtgctagg ctgctagcta gggaactgga     1140
tcctggaacg tggaggaggc aagtccggta tgctaagtac tttaactttc cttcttcaca     1200
tccacctgat tcagattatt ttgatctaaa ttaacttgca aaaatatat gtgtgatatc      1260
catctactat aattgcttac aatcaaaatt atatgtgatt ttttttagtt tagaagattt     1320
atatgcacag taaatctgaa tgttcttcac atgcatgatt tagtttaact ttaaagagtt     1380
atactaacta gtcttgataa agagatcttt tggagcaaca ccaaacctcg tgaggtgttt     1440
tgcctacgga aaggttgtgc tatgtaatga ttattattag gatcaaagtt gtaggataaa     1500
cgtaaaacct tctcgatgta tcttttatac aacattgtag tttagttata tatggagaga     1560
gtgatttaac actttgtgtt taagagtaga ataagttatt ccacactcta gccaaacgaa     1620
ctatttggca aatatctcgc tagctggtga gagccagagc cgtggaaagt ctgtcttgct     1680
attaaggcac aagcatcaaa caggaacatt tagagccatg gaaaagtgat gtgtcgccta     1740
ccaatgggcc aactgctagc gatgtaataa tagcatccaa gttgattttt tatagaacat     1800
gcaaggcgtt ggcaagtggg aaaatgattg atcgctggca agcttaactc tcggaactta     1860
tagcattcaa ctgaatcaga acaaagatta aaaaaaaata catttccatc gatagtgaaa     1920
aattattcaa ttgagtgaca acgaaaatca tattggaatg tacatttact tgttgatttt     1980
aaattagagg catttttcta ccttttttag ttaataagat atgcatatac ccacccttag     2040
tgttttcgag acaacgagag ggcacattgc ttttggtgct accatctctc tcaagcctca     2100
aataagttgt gcggacacga ttatcttccc gcgttggaat atcgtggcct ggtagagcta     2160
gcgaaaaatc ttccatgttg gaatatgtcg gcagccggat agccgccatg catgtaaagt     2220
ctctttttacc tttacacttg ctcaagtgac actgtatgtc gcctaccact tgctaaatca     2280
atgggccaac tgctagcgac gtaatagtag caagttgatt tacagtgttt tgctacagtt     2340
ctctgactt  gtttcttcat tttagactag ctgactactg tcgcttacct gccttccctt     2400
ctccacgtta gaggatccag ttctgatatt gagacctcga cgatgggagg aagggcgcga     2460
tcgatgtgga gtaatttgaa tttcaaatct atctatctgg ggtatattgg tccttcaccg     2520
atgtttgggg ggctgtcgga aattggttcc gcgatctaca aaagtgaatg gagggagtag     2580
ttgtttctcc aatccgtacc aacgcacgtg tttctaacta gtacttactt ccttcgcacc     2640
acaatatgga atagagggag tatcgataaa ctaacaaaga tgattactta cccggtttaa     2700
atgattcaag agctcattta atttggcact catcatttca tatatctttt ttggtagaaa     2760
tgaaataaag cagatctaga cactagctaa aaagtcgatg tagccttgtt atttccttgg     2820
gccacgcggg ccgggtgtgg tgctccctgc tctgtgtata aatggagatc aacatccaag     2880
gcctcctccc acacacacac gctacagagc agagcagagt cttgctccag tatctgccct     2940
ctcctgcctg cctgtagagc atccatcacg tgaagttcac ggacaaacta cgtacacagg     3000
cagctagctc tcgaaacctc gctcgaaacg cacctgcaga tcgctctctt cgtcgtcgtc     3060
gccgcgatca tcatcaacag ctccgtctgc cttggagcca cggccgtcca cgacgccgcc     3120
gcctcaggtc agtcgtcgga cggtgtccgt tcatttcctc cccattttg taattgatta      3180
acttgttata catgctgacc tcgacctgct gaataacgtc cgtccatggt ttcccgtcca     3240
```

```
ggcaccccgg gctgcaggaa ttcaccacca caccactcca ccagtaagaa gtgcagcagg   3300
tagctagtaa gccggcgtag ctttgctctt gcagctagct agctaaccat ggccgcctct   3360
gcctcttgcc tttctcttgt ggtgctcgtg gctctggcca cggcggcgtc ggcgcagctg   3420
tcaccgacct tctacgacac gtcctgcccc agggccctgg ccatcatcaa gagtggcgtc   3480
atggccgccg tgagcagcga ccctcggatg ggcgcgtcgc tgctccggct gcacttccac   3540
gactgcttcg tccaaggctg cgacgcgtct gttttgctgt ctggcatgga acaaaatgct   3600
atcccgaacg cggggtcgct gaggggcttc ggcgtcatcg acagcatcaa gacgcagatc   3660
gaggccatct gcaatcagac cgtctcctgc gccgacatcc tcaccgtcgc cgcccgtgac   3720
tccgttgtag ccctcggagg gccgtcatgg acagtccctc tggggagaag agattccaca   3780
gatgcaaacg aggcggcggc aaacagcgac ctgccaggct ttacatctag ccggtcagat   3840
cttgagctgg cattcagaaa caagggcctc cttacgatcg acatggtggc cctctcgggc   3900
gcgcacacca tcgccaggc gcagtgtggg acctttaagg acaggatcta caatgagact   3960
aacatcgaca cggccttcgc cacatctctc cgggccaact gccccaggtc aaacggcgac   4020
gggagcctgg cgaacctgga cacgacgacg gccaacacgt tcgataacgc ctactacacc   4080
aacctcatgt cacagaaggg gctcctgcac tcggaccagg tgctgttcaa caacgacacc   4140
accgacaaca ctgtccggaa cttttgcgtcg aacccagcgg cgttcagcag cgccttcacg   4200
accgccatga tcaagatggg caacatcgcg ccgaagacag gcacgcaggg gcagatcagg   4260
ctcagctgct ccagggtgaa ctcgtgattg atagacgagt tactgcatac tagccagcac   4320
gacacgtacg tgaatgaata aggccacaga accagtggcc aatataaata ccagctcttg   4380
aaaccgtgta ttttatgtac gagtagcagc aaatcatgca tgcatctaca catatatatg   4440
taacgatcga attcccactt tctcatgcaa aggcatggag aattactatc aatcttagtt   4500
atacgtgtat aaaaagcggc cgcgaattcg atatcaagct tatcgatacc gtcgacctcg   4560
acctgcaggc atgcccgctg aaatcaccag tctctctcta caaatctatc tctctctata   4620
ataatgtgtg agtagttccc agataaggga attagggttc ttataggggtt tcgctcatgt   4680
gttgagcata taagaaaccc ttagtatgta tttgtatttg taaaatactt ctatcaataa   4740
aatttctaat tcctaaaacc aaaatccagg ggtaccgagc tcgaattcta gtctacgcgg   4800
ccgcgagctc cagcttttgt tccctttagt gagggttaat tgcgcgcttg gcgtaatcat   4860
ggtcatagct gtttcctgtg tgaaattgtt atccgctcac aattccacac aacatacgag   4920
ccggaagcat aaagtgtaaa gcctggggtg cctaatgagt gagctaactc acattaattg   4980
cgttgcgctc actgcccgct ttccagtcgg gaaacctgtc gtgccagctg cattaatgaa   5040
tcggccaacg cgcggggaga ggcggtttgc gtattgggcg ctcttccgct tcctcgctca   5100
ctgactcgct gcgctcggtc gttcggctgc ggcgagcggt atcagctcac tcaaaggcgg   5160
taatacggtt atccacagaa tcaggggata acgcaggaaa gaacatgtga gcaaaaggcc   5220
agcaaaaggc caggaaccgt aaaaaggccg cgttgctggc gtttttccat aggctccgcc   5280
cccctgacga gcatcacaaa aatcgacgct caagtcagag gtggcgaaac ccgacaggac   5340
tataaagata ccaggcgttt ccccctggaa gctccctcgt gcgctctcct gttccgaccc   5400
tgccgcttac cggatacctg tccgcctttc tcccttcggg aagcgtggcg ctttctcata   5460
gctcacgctg taggtatctc agttcggtgt aggtcgttcg ctccaagctg ggctgtgtgc   5520
acgaaccccc cgttcagccc gaccgctgcg ccttatccgg taactatcgt cttgagtcca   5580
acccggtaag acacgactta tcgccactgg cagcagccac tggtaacagg attagcagag   5640
```

```
cgaggtatgt aggcggtgct acagagttct tgaagtggtg gcctaactac ggctacacta   5700
gaaggacagt atttggtatc tgcgctctgc tgaagccagt taccttcgga aaaagagttg   5760
gtagctcttg atccggcaaa caaaccaccg ctggtagcgg tggttttttt gtttgcaagc   5820
agcagattac gcgcagaaaa aaaggatctc aagaagatcc tttgatcttt tctacggggt   5880
ctgacgctca gtggaacgaa aactcacgtt aagggatttt ggtcatgaga ttatcaaaaa   5940
ggatcttcac ctagatcctt ttaaattaaa aatgaagttt taaatcaatc taaagtatat   6000
atgagtaaac ttggtctgac agttaccaat gcttaatcag tgaggcacct atctcagcga   6060
tctgtctatt tcgttcatcc atagttgcct gactccccgt cgtgtagata actacgatac   6120
gggagggctt accatctggc cccagtgctg caatgatacc gcgagaccca cgctcaccgg   6180
ctccagattt atcagcaata accagccagc cggaagggc cgagcgcaga agtggtcctg   6240
caactttatc cgcctccatc cagtctatta attgttgccg gaagctaga gtaagtagtt   6300
cgccagttaa tagtttgcgc aacgttgttg ccattgctac aggcatcgtg gtgtcacgct   6360
cgtcgtttgg tatggcttca ttcagctccg gttcccaacg atcaaggcga gttacatgat   6420
cccccatgtt gtgcaaaaaa gcggttagct ccttcggtcc tccgatcgtt gtcagaagta   6480
agttggccgc agtgttatca ctcatggtta tggcagcact gcataattct cttactgtca   6540
tgccatccgt aagatgcttt tctgtgactg gtgagtactc aaccaagtca ttctgagaat   6600
agtgtatgcg gcgaccgagt tgctcttgcc cggcgtcaat acgggataat accgcgccac   6660
atagcagaac tttaaaagtg ctcatcattg gaaaacgttc ttcggggcga aaactctcaa   6720
ggatcttacc gctgttgaga tccagttcga tgtaacccac tcgtgcaccc aactgatctt   6780
cagcatcttt tactttcacc agcgtttctg ggtgagcaaa aacaggaagg caaaatgccg   6840
caaaaaaggg aataagggcg acacggaaat gttgaatact catactcttc ctttttcaat   6900
attattgaag catttatcag ggttattgtc tcatgagcgg atacatattt gaatgtattt   6960
agaaaaataa acaaataggg gttccgcgca catttccccg aaaagtgcca c            7011
```

<210> SEQ ID NO 6
<211> LENGTH: 746
<212> TYPE: DNA
<213> ORGANISM: Triticum sp.

<400> SEQUENCE: 6

```
agcttattac atagcaagca tggggtactc caaaaccta gtagctggcc tgttcgcaat     60
gctgttacta gctccggccg tcttggccac cgacccagac cctctccagg acttctgtgt    120
cgccgacctc gacggcaagg cggtctcggt gaacgggcac acgtgcaagc ccatgtcgga    180
ggccggcgac gacttcctct tctcgtccaa gttggccaag gccggcaaca cgtccacccc    240
gaacggctcc gccgtgacgg agctcgacgt ggccgagtgg cccggtacca acacgctggg    300
tgtgtccatg aaccgcgtgg actttgctcc cggaggcacc aacccaccac acatccaccc    360
gcgtgccacc gagatcggca tcgtgatgaa aggtgagctt ctcgtgggaa tccttggcag    420
cctcgactcc gggaacaagc tctactcgag ggtggtgcgc gccggagaga cgttcctcat    480
cccacggggc ctcatgcact tccagttcaa cgtcggtaag accgaggcct ccatggtcgt    540
ctccttcaac agccagaacc ccggcattgt cttcgtgccc ctcacgctct tcggctccaa    600
cccgcccatc ccaacgccgg tgctcaccaa ggcactccgg gtggaggcca gggtcgtgga    660
acttctcaag tccaagtttg ccgctgggtt ttaatttcta ggagccttcc ctgaaatgat    720
```
aattatataa ttccatatat gcatgc                                                746

<210> SEQ ID NO 7
<211> LENGTH: 6452
<212> TYPE: DNA
<213> ORGANISM: Triticum sp.

<400> SEQUENCE: 7

| | |
|---|---|
| ctaaattgta agcgttaata ttttgttaaa attcgcgtta aattttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta aatcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgcgtaata cgactcacta tagggcgaat gggtaccgg | 660 |
| gccccccctc gagtctagaa ctagtggatc cccgacgccg aagtggagcc gacagccccc | 720 |
| aggtcccaag ccctcggcag actagatcac tagccctgga tcggcgaggt gactggatga | 780 |
| cgagcagcac ctggtctggc gggtgttggg cgagtagaac caggggcgat ggcgacgcgc | 840 |
| tgaccttctc ccctcaccgg cgatctgctc cttctgggtg ggggtcgccg gctgacgttc | 900 |
| tgttgcgggg tggggtcgc cggctggcgt tctgctgcgg ggtgggagtc gccgaccggc | 960 |
| gtgctgctgc taggacaatc ggtgaggcca gttaggtgct agccgatcga ttggcgaaga | 1020 |
| gatccgagtc ctggggagat cagtgaggcc aggtgctatt tggcctatca attggccagg | 1080 |
| ttctgggaac ggggcgtggc gtgatcaacg aggtgctagg ctgctagcta gggaactgga | 1140 |
| tcctggaacg tggaggaggc aagtccggta tgctaagtac tttaactttc cttcttcaca | 1200 |
| tccacctgat tcagattatt ttgatctaaa ttaacttgca aaaatatat gtgtgatatc | 1260 |
| catctactat aattgcttac aatcaaaatt atatgtgatt ttttttagtt tagaagattt | 1320 |
| atatgcacag taaatctgaa tgttcttcac atgcatgatt tagtttaact ttaaagagtt | 1380 |
| atactaacta gtcttgataa agagatcttt tggagcaaca ccaaacctcg tgaggtgttt | 1440 |
| tgcctacgga aaggttgtgc tatgtaatga ttattattag gatcaaagtt gtaggataaa | 1500 |
| cgtaaaacct tctcgatgta tcttttatac aacattgtag tttagttata tatggagaga | 1560 |
| gtgatttaac actttgtgtt taagagtaga ataagttatt ccacactcta gccaaacgaa | 1620 |
| ctatttggca aatatctcgc tagctggtga gagccagagc cgtggaaagt ctgtcttgct | 1680 |
| attaaggcac aagcatcaaa caggaacatt tagagccatg gaaaagtgat gtgtcgccta | 1740 |
| ccaatgggcc aactgctagc gatgtaataa tagcatccaa gttgattttt tatagaacat | 1800 |
| gcaaggcgtt ggcaagtggg aaaatgattg atcgctggca agcttaactc tcggaactta | 1860 |
| tagcattcaa ctgaatcaga acaaagatta aaaaaaaata catttccatc gatagtgaaa | 1920 |
| aattattcaa ttgagtgaca acgaaaatca tattggaatg tacatttact tgttgatttt | 1980 |
| aaattagagg cattttccta cctttttttag ttaataagat atgcatatac ccacccttag | 2040 |
| tgttttcgag acaacgagag ggcacattgc ttttggtgct accatctctc tcaagcctca | 2100 |

```
aataagttgt gcggacacga ttatcttccc gcgttggaat atcgtggcct ggtagagcta   2160
gcgaaaaatc ttccatgttg aatatgtcg gcagccggat agccgccatg catgtaaagt    2220
ctcttttacc tttacacttg ctcaagtgac actgtatgtc gcctaccact tgctaaatca   2280
atgggccaac tgctagcgac gtaatagtag caagttgatt tacagtgttt tgctacagtt   2340
ctctgacttt gtttcttcat tttagactag ctgactactg tcgcttacct gccttccctt   2400
ctccacgtta gaggatccag ttctgatatt gagacctcga cgatgggagg aagggcgcga   2460
tcgatgtgga gtaatttgaa tttcaaatct atctatctgg ggtatattgg tccttcaccg   2520
atgtttgggg ggctgtcgga aattggttcc gcgatctaca aaagtgaatg gagggagtag   2580
ttgtttctcc aatccgtacc aacgcacgtg tttctaacta gtacttactt ccttcgcacc   2640
acaatatgga atagagggag tatcgataaa ctaacaaaga tgattactta cccggtttaa   2700
atgattcaag agctcattta atttggcact catcatttca tatatctttt ttggtagaaa   2760
tgaaataaag cagatctaga cactagctaa aaagtcgatg tagccttgtt atttccttgg   2820
gccacgcggg ccggggtgtgg tgctccctgc tctgtgtata aatggagatc aacatccaag   2880
gcctcctccc acacacacac gctacagagc agagcagagt cttgctccag tatctgccct   2940
ctcctgcctg cctgtagagc atccatcacg tgaagttcac ggacaaacta cgtacacagg   3000
cagctagctc tcgaaacctc gctcgaaacg cacctgcaga tcgctctctt cgtcgtcgtc   3060
gccgcgatca tcatcaacag ctccgtctgc cttggagcca cggccgtcca cgacgccgcc   3120
gcctcaggtc agtcgtcgga cggtgtccgt tcatttcctc cccattttg taattgatta    3180 acttgttata catgctgacc tcgacctgct gaataacgtc cgtccatggt ttcccgtcca   3240
ggcaccccgg gggatccagc ttattacata gcaagcatgg ggtactccaa acccctagta   3300
gctggcctgt tcgcaatgct gttactagct ccggccgtct tggccaccga cccagaccct   3360
ctccaggact tctgtgtcgc cgacctcgac ggcaaggcgg tctcggtgaa cgggcacacg   3420
tgcaagccca tgtcggaggc cggcgacgac ttcctcttct cgtccaagtt ggccaaggcc   3480
ggcaacacgt ccaccccgaa cggctccgcc gtgacggagc tcgacgtggc cgagtggccc   3540
ggtaccaaca cgctgggtgt gtccatgaac cgcgtggact ttgctcccgg aggcaccaac   3600
ccaccacaca tccacccgcg tgccaccgag atcggcatcg tgatgaaagg tgagcttctc   3660
gtgggaatcc ttggcagcct cgactccggg aacaagctct actcgagggt ggtgcgcgcc   3720
ggagagacgt tcctcatccc acggggcctc atgcacttcc agttcaacgt cggtaagacc   3780
gaggcctcca tggtcgtctc cttcaacagc cagaaccccg gcattgtctt cgtgcccctc   3840
acgctcttcg gctccaaccc gcccatccca acgccggtgc tcaccaaggc actccgggtg   3900
gaggccaggg tcgtggaact tctcaagtcc aagtttgccg ctgggttta atttctagga    3960 gccttccctg aaatgataat tatataattc catatatgca tgcctgcagg catgcccgct   4020
gaaatcacca gtctctctct acaaatctat ctctctctat aataatgtgt gagtagttcc   4080
cagataaggg aattagggtt cttatagggt ttcgctcatg tgttgagcat ataagaaacc   4140
cttagtatgt atttgtattt gtaaaatact tctatcaata aaatttctaa ttcctaaaac   4200
caaaatccag gggtaccgag ctcgaattct agtctacgcg gccgcgagct ccagcttttg   4260
ttccctttag tgagggttaa ttgcgcgctt ggcgtaatca tggtcatagc tgtttcctgt   4320
gtgaaattgt tatccgctca caattccaca acaacatacga gccggaagca taaagtgtaa   4380
agcctggggt gcctaatgag tgagctaact cacattaatt gcgttgcgct cactgcccgc   4440
```

```
tttccagtcg ggaaacctgt cgtgccagct gcattaatga atcggccaac gcgcggggag   4500
aggcggtttg cgtattgggc gctcttccgc ttcctcgctc actgactcgc tgcgctcggt   4560
cgttcggctg cggcgagcgg tatcagctca ctcaaaggcg gtaatacggt tatccacaga   4620
atcaggggat aacgcaggaa agaacatgtg agcaaaaggc cagcaaaagg ccaggaaccg   4680
taaaaaggcc gcgttgctgg cgttttttcca taggctccgc cccctgacg agcatcacaa   4740 aaatcgacgc tcaagtcaga ggtggcgaaa cccgacagga ctataaagat accaggcgtt   4800
tccccctgga agctccctcg tgcgctctcc tgttccgacc ctgccgctta ccggatacct   4860
gtccgccttt ctcccttcgg gaagcgtggc gctttctcat agctcacgct gtaggtatct   4920
cagttcggtg taggtcgttc gctccaagct gggctgtgtg cacgaaccccc ccgttcagcc   4980 cgaccgctgc gccttatccg gtaactatcg tcttgagtcc aacccggtaa gacacgactt   5040
atcgccactg gcagcagcca ctggtaacag gattagcaga gcgaggtatg taggcggtgc   5100
tacagagttc ttgaagtggt ggcctaacta cggctacact agaaggacag tatttggtat   5160
ctgcgctctg ctgaagccag ttaccttcgg aaaaagagtt ggtagctctt gatccggcaa   5220
acaaaccacc gctggtagcg gtggttttt tgtttgcaag cagcagatta cgcgcagaaa   5280
aaaaggatct caagaagatc ctttgatctt ttctacgggg tctgacgctc agtggaacga   5340
aaactcacgt taagggattt tggtcatgag attatcaaaa aggatcttca cctagatcct   5400
tttaaattaa aaatgaagtt ttaaatcaat ctaaagtata tatgagtaaa cttggtctga   5460
cagttaccaa tgcttaatca gtgaggcacc tatctcagcg atctgtctat ttcgttcatc   5520
catagttgcc tgactccccg tcgtgtagat aactacgata cgggagggct taccatctgg   5580
ccccagtgct gcaatgatac cgcgagaccc acgctcaccg gctccagatt tatcagcaat   5640
aaaccagcca gccggaaggg ccgagcgcag aagtggtcct gcaactttat ccgcctccat   5700
ccagtctatt aattgttgcc gggaagctag agtaagtagt tcgccagtta atagtttgcg   5760
caacgttgtt gccattgcta caggcatcgt ggtgtcacgc tcgtcgtttg gtatggcttc   5820
attcagctcc ggttcccaac gatcaaggcg agttacatga tcccccatgt tgtgcaaaaa   5880
agcggttagc tccttcggtc ctccgatcgt tgtcagaagt aagttggccg cagtgttatc   5940
actcatggtt atggcagcac tgcataattc tcttactgtc atgccatccg taagatgctt   6000
ttctgtgact ggtgagtact caaccaagtc attctgagaa tagtgtatgc ggcgaccgag   6060
ttgctcttgc ccggcgtcaa tacgggataa taccgcgcca catagcagaa ctttaaaagt   6120
gctcatcatt ggaaaacgtt cttcggggcg aaaactctca aggatcttac cgctgttgag   6180
atccagttcg atgtaaccca ctcgtgcacc caactgatct tcagcatctt ttactttcac   6240
cagcgtttct gggtgagcaa aaacaggaag gcaaatgccg caaaaaagg gaataagggc   6300 gacacggaaa tgttgaatac tcatactctt cctttttcaa tattattgaa gcatttatca   6360
gggttattgt ctcatgagcg gatacatatt tgaatgtatt tagaaaaata aacaaatagg   6420
ggttccgcgc acatttcccc gaaaagtgcc ac                                 6452
```

<210> SEQ ID NO 8
<211> LENGTH: 1939
<212> TYPE: DNA
<213> ORGANISM: Triticum sp.

<400> SEQUENCE: 8

```
ccactgtcca cacgaaatgt gccatctgaa acgcgttctg gaacagcgtc aggtgtatga     60
agaagaggac ccagtcgggg cggtggaacc agaagaactt gttgctgggc tcgaccacgg    120
```

```
gtgccccctt gatgacgctc gaccggtcct ggatctccag ggccatctcc atgatgatca      180
tctctagctt ggttccaaca cacaagagga tgatgagagg gatgaaagaa acccaggtga      240
gtgtgccgat cccgtcgata tcaaggaaga gggtgaggat cgccacagcc cacagcggga      300
ggctgcgaaa agaggccaaa tgtgtcaaga tcatgcaaca aggaccagca ggggcaaaga      360
ccatgacgca gcaaactgat agtattgtat catatggaag ctaagcaata tcatatggag      420
cctgacgaca ctcgtgccga attcgattcg tgaatttcta gagaacaaaa ggtatgcatc      480
aatttagaaa aaagtacact attatgtgat gtttgtttcc tatgctagtg aacggatta       540 gaattttttt ttcattaagg tcacctttac tggcataagc agttcacact aaacggtaaa      600
ccttataggt gaaaattttc aggcatatat atatatatat atatatatat atgtttgatt      660
ctttccggct taacaaaata attagcaagt acttcttgtt gcatttgttc caacggctga      720
atttattggc atcggtccaa gaaatccatc taaatgtttt acatttcacc aaagtgtgtg      780
tcatgacaga tgtaacaaat aataaaccaa aaggagagga aggaaagagg aagataaatg      840
ttacaaaaat ttaaatcaaa cttatttcta cctttctcct tacctaccca gtttaaaaac      900
acatattata ttttaaagag aggcaacatg cgccaaaggc tacccttgaa aattcctaaa      960
atattgtaca tttgactgat gaccaaacaa aaagttaaat tgtctcttcc ttatcacatt     1020
atatttccat gcatgccttt ttctggaaac ttactatcag caaaatttag atgaaaggat     1080
aatgccacat aatttcagtc tccaagagat ttgttagttg tcatatatta aattggtggg     1140
ccaatctatt cctgggtctt tttatgtatc tacttgacca tttgaacttc tgtagttaat     1200
tgtattctat gaatgatcac tcatccaaaa acttgttatt tgtgttttac tctgttgaat     1260
cttgaatatt tattcatttt gttcatcata cgattggagg cccataatag atgcttaatg     1320
agagtaagat tatcgatctc caaacacatg cttcttacta gtgttgaata tatacccttt     1380
tagatgtata gttcaaccca tagattcata tgaccctcag ctttctgatg tgtatgtatg     1440
accttacact gacactctga actaatgtag gtatcttgtc ctgcaggaat tcggcacgag     1500
tgtcgtcagg ctccatatga tattgcttag cttccatatg atacaatact atcagtttgc     1560
tgcgtcatgg tctttgcccc tgctggtcct tgttgcatga tcttgacaca tttggcctct     1620
tttcgcagcc tcccgctgtg ggctgtggcg atcctcaccc tcttccttga tatcgacggg     1680
atcggcacac tcacctgggt ttctttcatc cctctcatca tcctcttgtg tgttggaacc     1740
aagctagaga tgatcatcat ggagatggcc ctggagatcc aggaccggtc gagcgtcatc     1800
aagggggcac ccgtggtcga gcccagcaac aagttcttct ggttccaccg ccccgactgg     1860
gtcctcttct tcatacacct gacgctgttc cagaacgcgt ttcagatggc acatttcgtg     1920
tggacaggca tgcgactgg                                                   1939
```

<210> SEQ ID NO 9
<211> LENGTH: 7633
<212> TYPE: DNA
<213> ORGANISM: Triticum sp.

<400> SEQUENCE: 9

```
ctaaattgta agcgttaata tttgttaaa attcgcgtta aattttgtt aaatcagctc        60 atttttaac caataggccg aaatcggcaa atcccttat aaatcaaaag aatagaccga       120
gatagggttg agtgttgttc cagtttggaa caagagtcca ctattaaaga acgtggactc      180
caacgtcaaa gggcgaaaaa ccgtctatca gggcgatggc ccactacgtg aaccatcacc      240
```

```
ctaatcaagt tttttggggt cgaggtgccg taaagcacta aatcggaacc ctaaagggag      300
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta tagggcgaat gggtaccgg       660 gcccccctc gagtctagaa ctagtggatc cccgacgccg aagtgagcc gacagccccc        720 aggtcccaag ccctcggcag actagatcac tagccctgga tcggcgaggt gactggatga     780
cgagcagcac ctggtctggc gggtgttggg cgagtagaac caggggcgat ggcgacgcgc     840
tgaccttctc ccctcaccgg cgatctgctc cttctgggtg ggggtcgccg gctgacgttc     900
tgttgcgggg tggggtcgc cggctggcgt tctgctgcgg ggtgggagtc gccgaccggc      960
gtgctgctgc taggacaatc ggtgaggcca gttaggtgct agccgatcga ttggcgaaga    1020
gatccgagtc ctggggagat cagtgaggcc aggtgctatt tggcctatca attggccagg    1080
ttctgggaac ggggcgtggc gtgatcaacg aggtgctagg ctgctagcta gggaactgga    1140
tcctggaacg tggaggaggc aagtccggta tgctaagtac tttaactttc cttcttcaca    1200
tccacctgat tcagattatt ttgatctaaa ttaacttgca aaaatatat gtgtgatatc      1260 catctactat aattgcttac aatcaaaatt atatgtgatt ttttttagtt tagaagattt    1320
atatgcacag taaatctgaa tgttcttcac atgcatgatt tagtttaact ttaaagagtt    1380
atactaacta gtcttgataa agagatcttt tggagcaaca ccaaacctcg tgaggtgttt    1440
tgcctacgga aaggttgtgc tatgtaatga ttattattag gatcaaagtt gtaggataaa    1500
cgtaaaacct tctcgatgta tcttttatac aacattgtag tttagttata tatggagaga    1560
gtgatttaac actttgtgtt taagagtaga ataagttatt ccacactcta gccaaacgaa    1620
ctatttggca aatatctcgc tagctggtga gagccagagc cgtggaaagt ctgtcttgct    1680
attaaggcac aagcatcaaa caggaacatt tagagccatg gaaaagtgat gtgtcgccta    1740
ccaatgggcc aactgctagc gatgtaataa tagcatccaa gttgattttt tatagaacat    1800
gcaaggcgtt ggcaagtggg aaaatgattg atcgctggca agcttaactc tcggaactta    1860
tagcattcaa ctgaatcaga acaaagatta aaaaaaaata catttccatc gatagtgaaa    1920
aattattcaa ttgagtgaca acgaaaatca tattggaatg tacatttact tgttgatttt    1980
aaattagagg cattttttcta cctttttag ttaataagat atgcatatac ccacccttag    2040
tgttttcgag acaacgagag ggcacattgc ttttggtgct accatctctc tcaagcctca    2100
aataagttgt gcggacacga ttatcttccc gcgttggaat atcgtggcct ggtagagcta    2160
gcgaaaaatc ttccatgttg gaatatgtcg gcagccggat agccgccatg catgtaaagt    2220
ctcttttacc tttacacttg ctcaagtgac actgtatgtc gcctaccact tgctaaatca    2280
atgggccaac tgctagcgac gtaatagtag caagttgatt tacagtgttt tgctacagtt    2340
ctctgacttt gtttcttcat tttagactag ctgactactg tcgcttacct gccttccctt    2400
ctccacgtta gaggatccag ttctgatatt gagacctcga cgatgggagg aagggcgcga    2460
tcgatgtgga gtaatttgaa tttcaaatct atctatctgg ggtatattgg tccttcaccg    2520
atgtttgggg ggctgtcgga aattggtcc gcgatctaca aaagtgaatg gagggagtag     2580
ttgtttctcc aatccgtacc aacgcacgtg tttctaacta gtacttactt ccttcgcacc    2640
```

```
acaatatgga atagagggag tatcgataaa ctaacaaaga tgattactta cccggtttaa    2700
atgattcaag agctcattta atttggcact catcatttca tatatctttt ttggtagaaa    2760
tgaaataaag cagatctaga cactagctaa aaagtcgatg tagccttgtt atttccttgg    2820
gccacgcggg ccgggtgtgg tgctccctgc tctgtgtata aatggagatc aacatccaag    2880
gcctcctccc acacacacac gctacagagc agagcagagt cttgctccag tatctgccct    2940
ctcctgcctg cctgtagagc atccatcacg tgaagttcac ggacaaacta cgtacacagg    3000
cagctagctc tcgaaacctc gctcgaaacg cacctgcaga tcgctctctt cgtcgtcgtc    3060
gccgcgatca tcatcaacag ctccgtctgc cttggagcca cggccgtcca cgacgccgcc    3120
gcctcaggtc agtcgtcgga cggtgtccgt tcatttcctc cccattttg taattgatta     3180 acttgttata catgctgacc tcgacctgct gaataacgtc cgtccatggt ttcccgtcca    3240
ggcaccccgg ccactgtcc acgaaatg tgccatctga aacgcgttct ggaacagcgt       3300
caggtgtatg aagaagagga cccagtcggg gcggtggaac cagaagaact tgttgctggg    3360
ctcgaccacg ggtgcccct tgatgacgct cgaccggtcc tggatctcca gggccatctc     3420
catgatgatc atctctagct tggttccaac acacaagagg atgatgagag ggatgaaaga    3480
aacccaggtg agtgtgccga tcccgtcgat atcaaggaag agggtgagga tcgccacagc    3540
ccacagcggg aggctgcgaa aagaggccaa atgtgtcaag atcatgcaac aaggaccagc    3600
aggggcaaag accatgacgc agcaaactga tagtattgta tcatatggaa gctaagcaat    3660
atcatatgga gcctgacgac actcgtgccg aattcgattc gtgaatttct agagaacaaa    3720
aggtatgcat caatttagaa aaaagtacac tattatgtga tgtttgtttc ctatgctagt    3780
ggaacggatt agaattttt tttcattaag gtcacctta ctggcataag cagttcacac      3840
taaacggtaa accttatagg tgaaaatttt caggcatata tatatatata tatatata     3900 tatgtttgat tctttccggc ttaacaaat aattagcaag tacttcttgt tgcatttgtt     3960
ccaacggctg aatttattgg catcggtcca agaaatccat ctaaatgttt tacatttcac    4020
caaagtgtgt gtcatgacag atgtaacaaa taataaacca aaaggagagg aaggaaagag    4080
gaagataaat gttacaaaaa tttaaatcaa acttatttct accttctcc ttacctaccc     4140 agtttaaaaa cacatattat attttaaaga gaggcaacat gcgccaaagg ctacccttga    4200
aaattcctaa aatattgtac atttgactga tgaccaaaca aaagttaaa ttgtctcttc     4260 cttatcacat tatatttcca tgcatgcctt tttctggaaa cttactatca gcaaaattta    4320
gatgaaagga taatgccaca taatttcagt ctccaagaga tttgttagtt gtcatatatt    4380
aaattggtgg gccaatctat tcctgggtct ttttatgtat ctacttgacc atttgaactt    4440
ctgtagttaa ttgtattcta tgaatgatca ctcatccaaa aacttgttat ttgtgttta     4500 ctctgttgaa tcttgaatat ttattcattt tgttcatcat acgattggag gcccataata    4560
gatgcttaat gagagtaaga ttatcgatct ccaaacacat gcttcttact agtgttgaat    4620 atatacccttt ttagatgtat agttcaaccc atagattcat atgaccctca gctttctgat   4680
gtgtatgtat gaccttacac tgacactctg aactaatgta ggtatcttgt cctgcaggaa    4740
ttcggcacga gtgtcgtcag gctccatatg atattgctta gcttccatat gatacaatac    4800
tatcagtttg ctgcgtcatg gtctttgccc ctgctggtcc ttgttgcatg atcttgacac    4860
atttggcctc ttttcgcagc ctcccgctgt gggctgtggc gatcctcacc ctcttccttg    4920
atatcgacgg gatcggcaca ctcacctggg tttctttcat ccctctcatc atcctcttgt    4980
```

-continued

```
gtgttggaac caagctagag atgatcatca tggagatggc cctggagatc caggaccggt    5040
cgagcgtcat caaggggggca cccgtggtcg agcccagcaa caagttcttc tggttccacc    5100
gccccgactg ggtcctcttc ttcatacacc tgacgctgtt ccagaacgcg tttcagatgg    5160
cacatttcgt gtggacaggc atgcgactgg gcatgcccgc tgaaatcacc agtctctctc    5220
tacaaatcta tctctctcta taataatgtg tgagtagttc ccagataagg gaattagggt    5280
tcttataggg tttcgctcat gtgttgagca tataagaaac ccttagtatg tatttgtatt    5340
tgtaaaatac ttctatcaat aaaatttcta attcctaaaa ccaaaatcca ggggtaccga    5400
gctcgaattc tagtctacgc ggccgcgagc tccagctttt gttccccttta gtgagggtta    5460 attgcgcgct tggcgtaatc atggtcatag ctgtttcctg tgtgaaattg ttatccgctc    5520
acaattccac acaacatacg agccggaagc ataaagtgta aagcctgggg tgcctaatga    5580
gtgagctaac tcacattaat tgcgttgcgc tcactgcccg ctttccagtc gggaaacctg    5640
tcgtgccagc tgcattaatg aatcggccaa cgcgcgggga gaggcggttt gcgtattggg    5700
cgctcttccg cttcctcgct cactgactcg ctgcgctcgg tcgttcggct gcggcgagcg    5760
gtatcagctc actcaaaggc ggtaatacgg ttatccacag aatcagggga taacgcagga    5820
aagaacatgt gagcaaaagg ccagcaaaag gccaggaacc gtaaaaaggc cgcgttgctg    5880
gcgtttttcc ataggctccg ccccccctgac gagcatcaca aaaatcgacg ctcaagtcag    5940
aggtggcgaa acccgacagg actataaaga taccaggcgt ttccccctgg aagctccctc    6000
gtgcgctctc ctgttccgac cctgccgctt accggatacc tgtccgcctt tctcccttcg    6060
ggaagcgtgg cgctttctca tagctcacgc tgtaggtatc tcagttcggt gtaggtcgtt    6120
cgctccaagc tgggctgtgt gcacgaaccc cccgttcagc ccgaccgctg cgccttatcc    6180
ggtaactatc gtcttgagtc aacccggta agacacgact tatcgccact ggcagcagcc    6240
actggtaaca ggattagcag agcgaggtat gtaggcggtg ctacagagtt cttgaagtgg    6300
tggcctaact acggctacac tagaaggaca gtatttggta tctgcgctct gctgaagcca    6360
gttaccttcg gaaaaagagt tggtagctct tgatccggca acaaaccac cgctggtagc    6420 ggtggttttt ttgtttgcaa gcagcagatt acgcgcagaa aaaaaggatc tcaagaagat    6480
cctttgatct tttctacggg gtctgacgct cagtggaacg aaaactcacg ttaagggatt    6540
ttggtcatga gattatcaaa aaggatcttc acctagatcc ttttaaatta aaaatgaagt    6600
tttaaatcaa tctaaagtat atatgagtaa acttggtctg acagttacca atgcttaatc    6660
agtgaggcac ctatctcagc gatctgtcta tttcgttcat ccatagttgc ctgactcccc    6720
gtcgtgtaga taactacgat acgggagggc ttaccatctg gccccagtgc tgcaatgata    6780
ccgcgagacc cacgctcacc ggctccagat ttatcagcaa taaaccagcc agccggaagg    6840
gccgagcgca gaagtggtcc tgcaacttta tccgcctcca tccagtctat taattgttgc    6900
cgggaagcta gagtaagtag ttcgccagtt aatagtttgc gcaacgttgt tgccattgct    6960
acaggcatcg tggtgtcacg ctcgtcgttt ggtatggctt cattcagctc cggttcccaa    7020
cgatcaaggc gagttacatg atcccccatg ttgtgcaaaa aagcggttag ctccttcggt    7080
cctccgatcg ttgtcagaag taagttggcc gcagtgttat cactcatggt tatggcagca    7140
ctgcataatt ctcttactgt catgccatcc gtaagatgct tttctgtgac tggtgagtac    7200
tcaaccaagt cattctgaga atagtgtatg cggcgaccga gttgctcttg cccggcgtca    7260
atacgggata taccgcgcc acatagcaga actttaaaag tgctcatcat tggaaaacgt    7320
tcttcggggc gaaaactctc aaggatctta ccgctgttga gatccagttc gatgtaaccc    7380
```

-continued

```
actcgtgcac ccaactgatc ttcagcatct tttactttca ccagcgtttc tgggtgagca      7440
aaaacaggaa ggcaaaatgc cgcaaaaaag ggaataaggg cgacacggaa atgttgaata      7500
ctcatactct tcctttttca atattattga agcatttatc agggttattg tctcatgagc      7560
ggatacatat ttgaatgtat ttagaaaaat aaacaaatag gggttccgcg cacatttccc      7620
cgaaaagtgc cac                                                        7633

<210> SEQ ID NO 10
<211> LENGTH: 30
<212> TYPE: DNA
<213> ORGANISM: Artificial Sequence
<220> FEATURE:
<223> OTHER INFORMATION: Adaptor primer

<400> SEQUENCE: 10
atatatctgc agggagccac ggccgtccac                                        30

<210> SEQ ID NO 11
<211> LENGTH: 27
<212> TYPE: DNA
<213> ORGANISM: Artificial Sequence
<220> FEATURE:
<223> OTHER INFORMATION: Adaptor primer

<400> SEQUENCE: 11
tatcccgggc ccgtgcctgg acgggaa                                           27

<210> SEQ ID NO 12
<211> LENGTH: 30
<212> TYPE: DNA
<213> ORGANISM: Artificial Sequence
<220> FEATURE:
<223> OTHER INFORMATION: Adaptor primer

<400> SEQUENCE: 12
atatatctcg agtctagaac tagtggatcc                                        30

<210> SEQ ID NO 13
<211> LENGTH: 30
<212> TYPE: DNA
<213> ORGANISM: Artificial Sequence
<220> FEATURE:
<223> OTHER INFORMATION: Adaptor primer

<400> SEQUENCE: 13
atatattacg tagtttgtcc gtgaacttca                                        30

<210> SEQ ID NO 14
<211> LENGTH: 41
<212> TYPE: DNA
<213> ORGANISM: Artificial Sequence
<220> FEATURE:
<223> OTHER INFORMATION: Oligonucleotide

<400> SEQUENCE: 14
gtacacaggc agctagctct cgaaacctcg ctcgaaacgc a                           41

<210> SEQ ID NO 15
<211> LENGTH: 41
<212> TYPE: DNA
<213> ORGANISM: Artificial Sequence
<220> FEATURE:
<223> OTHER INFORMATION: Oligonucleotide
```

```
-continued

<400> SEQUENCE: 15
catgtgtccg tcgatcgaga gctttggagc gagctttgcg t                    41
```